(12) United States Patent
Edwards

(10) Patent No.: US 6,743,197 B1
(45) Date of Patent: *Jun. 1, 2004

(54) TREATMENT OF DISCRETE TISSUES IN RESPIRATORY, URINARY, CIRCULATORY, REPRODUCTIVE AND DIGESTIVE SYSTEMS

(75) Inventor: Stuart D. Edwards, Portola Valley, CA (US)

(73) Assignee: Novasys Medical, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/347,441

(22) Filed: Jul. 2, 1999

Related U.S. Application Data

(63) Continuation-in-part of application No. 08/677,811, filed on Jul. 10, 1996, now Pat. No. 5,921,954.

(51) Int. Cl.[7] .............................................. A61M 31/00
(52) U.S. Cl. .................................. 604/103.01; 607/102
(58) Field of Search ............ 604/96.01, 103.01–103.02, 604/915, 20, 21; 606/192–194, 1, 27, 32–34; 607/1–3, 96–102, 115; 600/372–373, 381

(56) References Cited

U.S. PATENT DOCUMENTS

| | | | | |
|---|---|---|---|---|
| 5,499,971 A | * | 3/1996 | Shapland et al. | |
| 5,531,676 A | * | 7/1996 | Edwards et al. | 604/164.02 |
| 5,536,240 A | * | 7/1996 | Edwards et al. | 604/22 |
| 5,588,960 A | * | 12/1996 | Edwards et al. | 604/20 |
| 5,704,908 A | * | 1/1998 | Hofmann et al. | 604/21 |
| 5,733,319 A | * | 3/1998 | Neilson et al. | 607/105 |
| 5,840,076 A | * | 11/1998 | Swanson | |
| 6,009,877 A | * | 1/2000 | Edwards | 128/898 |
| 6,056,744 A | * | 5/2000 | Edwards | 606/41 |
| 6,425,877 B1 | * | 7/2002 | Edwards | 604/21 |
| 2001/0031941 A1 | * | 10/2001 | Edwards et al. | 604/22 |

* cited by examiner

Primary Examiner—LoAn H. Thanh
(74) Attorney, Agent, or Firm—Glenn Patent Group; Michael A. Glenn

(57) ABSTRACT

A method and system for treating body structures or tissue allows treatment by any of ablation, coating, expansion, plumping, shaping, and shrinking. Treatment sites include any of a sphincter, sinus or orifice. During treatment, electrodes emerge from apertures in a balloon. The balloon with liquid from a circulating bath cools tissue in direct contact with electrodes and immediately adjacent, so that discrete regions are treated, with minimal damage to adjacent structures. Sensors, coupled to electrodes, measure treatment properties such as: temperature, impedance and nervous activity. Measurements are used for: diagnostic assessment, determining treatment parameters, providing nervous stimulation and/or blocking, and feedback for controlling energy delivery. The catheter includes an optical path that can be coupled to external viewing apparatus. Endoscopic methods, including fluoroscopic, fiber optic, or radioscopy allow examining tissue and determining position of electrodes. The catheter includes a suction apparatus used to remove liquids obscuring treatment area and to gently conform treatment area to electrodes.

17 Claims, 18 Drawing Sheets

TREATMENT OF DISCRETE TISSUES IN RESPIRATORY, URINARY, CIRCULATORY, REPRODUCTIVE AND DIGESTIVE SYSTEMS

CROSS REFERENCE TO RELATED APPLICATION

This application is a Continuation-in-part of U.S. patent application Ser. No. 08/677,811, filed Jul. 10, 1996, now U.S. Pat. No. 5,921,954, issued Jul. 13, 1999, which document is hereby incorporated by reference as if fully set forth herein.

BACKGROUND OF THE INVENTION

1. Field of the Invention

This invention relates to treatment of tissue in the urinary, digestive, respiratory, reproductive and circulatory systems. Such treatment can be performed using ablation, coating, expansion, plumping, shaping, shrinking, or related techniques.

2. Related Art

Human beings and other animals such as livestock and small animals are subject to a number of disorders that affect the digestive, urinary, respiratory, circulatory and reproductive systems. Frequently, these disorders (such as urinary and fecal incontinence) involve the relative tone of sphincters and other muscles. Other disorders (such as aneurysms) involve changes in the integrity of the wall of an artery or other body structure. Still other disorders (such as cancers, hemorrhoids and pilonital cysts) involve uncontrolled or improperly regulated growth of tissue. Many other disorders, particularly reproductive disorders, involve occlusions in otherwise healthy tissue.

Known methods for the treatment of these disorders include surgery, pharmaceutical remedies, chemotherapeutic regimens, radiation, photodynamic therapy and lifestyle modification. These methods only occasionally achieve the goal of successful treatment of disorders in circulatory, urinary, respiratory, reproductive and digestive systems. Moreover, these methods suffer from several drawbacks.

Drawbacks to surgical treatment include its highly invasive nature, associated risks, possible iatrogenic effects, and high cost. Drawbacks to pharmaceutical and chemotherapeutic treatments include their relative ineffectiveness (particularly in the oral cavity and adjacent respiratory structures) and associated side effects. Moreover, these approaches are contraindicated for many patients. Drawbacks to lifestyle modification include relatively poor patient compliance and relative ineffectiveness. Drawbacks to photodynamic therapy include its frequent unavailability and limited applicability. Drawbacks to radiation include side effects such as exhaustion, radiation burns, chronic dry mouth and permanent distortion of the taste buds. Accordingly, it would be advantageous to provide techniques for treatment of these disorders that are not subject to these known drawbacks.

The use of radio frequency (RF) to ablate tissue in the body (such as heart muscle tissue) is known in the art of cardiac treatment. However, known systems that rely on RF energy are still subject to several drawbacks. One drawback is that it can be difficult to target very small areas of tissue for treatment without causing thermal damage to adjacent structures.

A second problem involves controlling the flow of bodily fluids and gases into an area of the body where tissue ablation is taking place. Controlling the flow of bodily fluids and gases is critical because they can dissipate and detrimentally absorb the energy to be applied to the tissue to be ablated.

A third problem in the art involves directing and positioning the electrodes in the body cavity or orifice. Difficulties in accurately positioning the electrodes in the target orifice detract from treatment. Frequently, unhealthy tissue remains untreated while healthy tissue is removed. Difficulties in directing and positioning the electrodes are particularly problematic because one of the goals of treatment is to minimize collateral damage to healthy tissue and to completely ablate diseased tissue.

A fourth problem in the art involves difficulty in the simultaneous use of complimentary technology. Known systems do not provide for optimal, simultaneous use of auxiliary tools for nerve stimulation, visualization, feedback technology and drug administration.

A fifth problem in the known art involves the simultaneous heating and cooling of adjacent tissues. Frequently, it is desirable to prevent thermal damage to adjacent tissues. One way of preventing such damage is by controlling the temperature of the adjacent tissues. Known systems to not provide for the simultaneous heating and cooling of adjacent tissues.

A sixth problem in the known art involves conforming the interior of an organ such as a bladder to as to be in optimal contact with the electrodes. This inability makes it difficult to predict with any accuracy the overall degree of shrinkage that may result from RF treatment.

Accordingly, it would be advantageous to provide improved techniques for treatment of disorders in the circulatory, respiratory, urinary, digestive and reproductive systems. For example, it would be advantageous to provide devices bearing different arrays of curvilinear or straight electrodes such that each electrode is surrounded by saline. It would be particularly advantageous if such devices could also support apparatus for drug administration and tissue visualization. Such devices would allow medical personnel to (1) visualize the tissue to be treated, (2) seal off the area from fluids and gases that would disturb the area to be treated, (3) target very small areas for treatment, (4) treat all diseased tissue while sparing healthy tissue and (5) provide for the localized administration of drugs to numb the area and treat the disorder. These advantages are achieved in an embodiment of the invention in which medical personnel use a catheter bearing multiple controls for visualization and drug administration, balloon-like air sacs for sealing the area and multiple arrays of curvilinear or straight electrodes that extend out of a holes in a multiporous balloon.

SUMMARY OF THE INVENTION

In one aspect of the invention, an environment proximate to or surrounding the targeted treatment region can be isolated or controlled by blocking the flow of gases or liquids using an inflatable, microporous balloon positioned immediately adjacent to the tissue that is to be ablated. The inflatable microporous balloon also serves to anchor the catheter in place and prevent the catheter from being expelled from-the body. The inflatable microporous balloon can also insure that locally administered drugs remain in the area where most needed.

In a second aspect of the invention, straight or curvilinear electrodes emerge out of small apertures in the balloon. Inflation of the balloon with liquid from a constantly circulating bath of chilled fluid has the effect of cooling tissue, including tissue that is immediate adjacent to tissue in direct contact with an electrode. This permits treatment of small, discrete regions while minimizing collateral damage to immediately adjacent structures.

In a third aspect of the invention, the electrodes are coupled to sensors that measure properties of the target region such as temperature, impedance and nervous activity. These measurements are useful both in making diagnostic assessments as well as in determining treatment parameters. Moreover, they can be used to provide for nervous stimulation and/or blocking, and permit the use of feedback technique to control delivery of the RF energy.

In a fourth aspect of the invention, the catheter includes an optical path that can be coupled to external viewing apparatus. A wide variety of endoscopic methods, including fluoroscopic, fiber optic, or radioscopic techniques can be used to examine tissue and determine the position of the electrodes in the body.

In a fifth aspect of the invention, the catheter includes suction apparatus. This suction apparatus can be used to draw away liquids that obscure the treatment area and to gently conform the treatment area to the electrode.

DETAILED DESCRIPTION OF THE PREFERRED EMBODIMENT

System Elements

Figure 1:
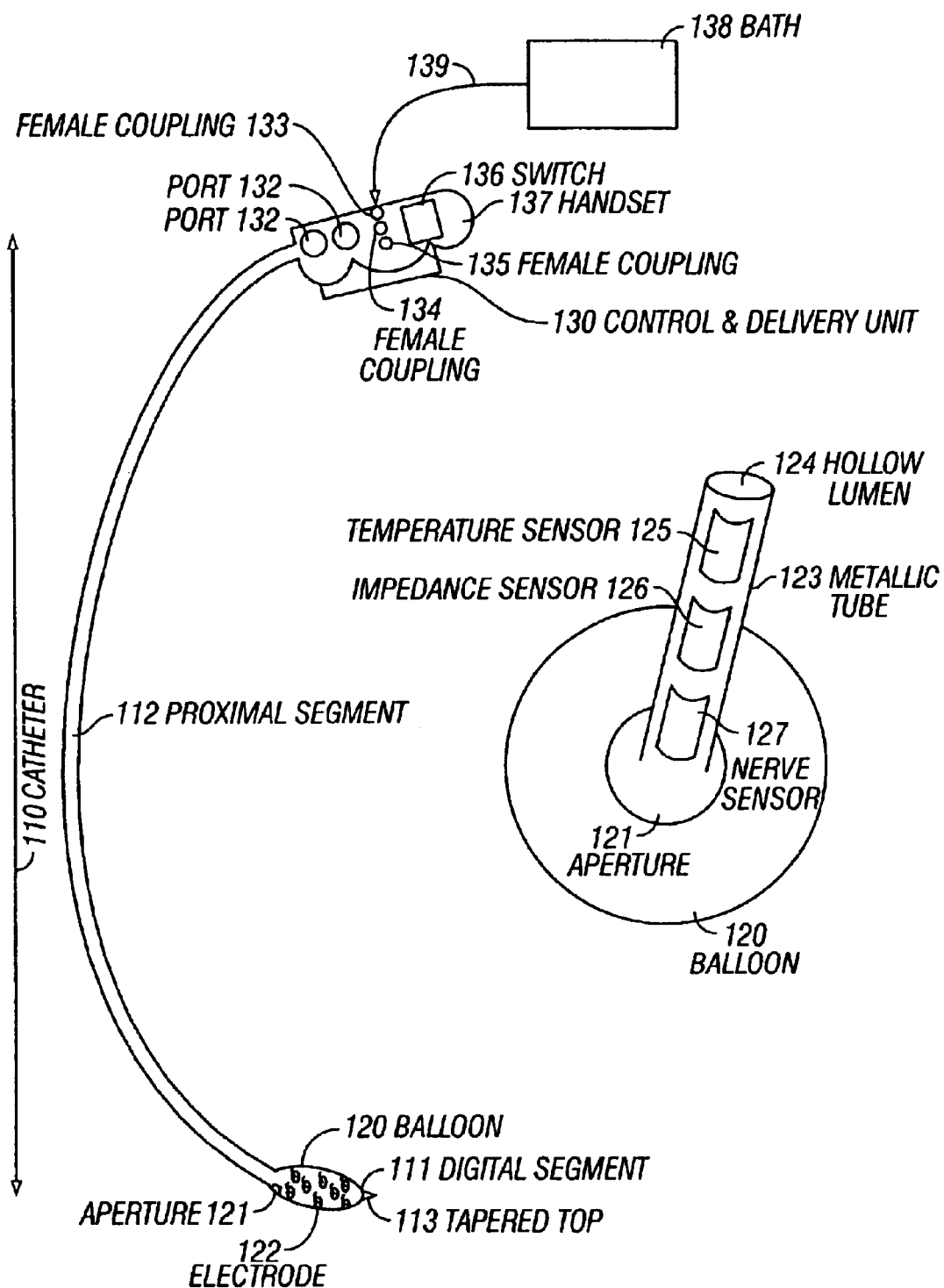
FIG. 1 is a block diagram of a system for ablating tissue using a catheter and electrode assembly.

FIG. 1 is a block diagram of a system for ablating tissue associated with the circulatory, respiratory, reproductive, digestive, auditory and urinary systems along with their related sphincters and associated musculature using a catheter and electrode assembly.

A catheter and electrode assembly 100 for treating tissue includes a catheter 110, an inflatable microporous balloon 120 and a control and delivery linkage 130.

The catheter 110 includes a short, distal segment 111 and a proximal segment 112. The distal segment includes a tapered tip 113 for easy insertion into an orifice, a surgically created opening such as a stoma, or though a herniated muscle, body shunt or incision made for the purpose of insertion. The tapered tip 113 may be either flexible or rigid depending upon the orifice or opening into which the catheter 110 is to be inserted. The overall length of the shaft of the catheter 110 (including the inflatable, microporous balloon 120) from the tapered tip 113 to the junction where the catheter 110 is coupled to the control and delivery linkage 130 is about 65 centimeters. The diameter of the catheter 110 is about 0.4 centimeters. In an alternative embodiment, the length and diameter of the shaft of the catheter 110 may vary substantially depending upon application and method of treatment.

Taken together, the distal segment 111, the inflatable, microporous balloon 120 and the proximal segment 112 are linearly contiguous and form one continuous unit.

The inflatable, microporous balloon 120 can be composed of a biologically non-reactive material that is resistant to high temperatures such as Kevlar. The balloon 120 is shaped so that it contains numerous sealed openings that create a set of apertures 121. These apertures 121 do not effect the integrity of the walls of the balloon 120 because they are sealed. This unique shape provides for simultaneous application of RF energy and cooling of tissue.

One or more electrodes 122 emerge through each member of the plurality of apertures 121. In a preferred embodiment, one electrode 122 emerges from every aperture 121. However, in alternative embodiments, two or more electrodes can emerge from a single aperture. Each electrode 122 includes a metallic tube 123 defining a hollow lumen 124, a temperature sensor 125, an impedance sensor 126, a sensor for measuring nervous activity 127, and a nerve sensor 128 that is responsive to individual nerves. In addition to ablating tissue by delivering RF energy, the electrodes 122 are disposed to deliver at least one flowable substance to the area where ablation is to take place. In a preferred embodiment, the flowable substance includes saline with a concentration of less than about 10% NaCl, which aids in hydration of body structures. However, in alternative embodiments, the deliverable, flowable liquids include other substances, including anesthetic drugs, anti-inflammatory agents, chemotherapeutic agents, systemic or topical antibiotics, collagen and radioactive substances such as labeled tracers. In alternative embodiments, the overall dimensions of the inflatable microporous balloon 120 can vary as long as they are responsive to the dimensions of the targeted tissue. For instance, the dimensions of an inflatable, microporous balloon 120 that is used to ablate tissue in a uterus will be larger than those of an inflatable microporous balloon 120 that is used to ablate tissue in a fallopian tube. In other alternative embodiments, the shape and length of the electrodes may also vary.

Exact positioning of the electrodes 122 is achieved through the use of visualization apparatus coupled to port 132.

Simultaneous application of RF energy and cooling is achieved by means of a temperature regulator such as inflating the balloon 120 with liquid from a continuously circulating bath of saline 138 whose temperature is controlled.

Manipulating the control and delivery linkage 130 operates the assembly 110. The control and delivery linkage 130 includes a port 131, a port 132, three female couplings 133, 134 and 135, a mechanical switch 136 and a hand set 137.

The port 131 can be coupled to a source of RF energy. The port 132 can be coupled to visualization apparatus, such as fiber optic devices, fluoroscopy equipment and related endoscopic apparatus, to allow internal viewing of the targeted tissue. In a preferred embodiment, female coupling 133 can be connected to biologically nonreactive tubing 139 containing at least a single lumen through the microporous balloon 120. Female coupling 134 can be connected to drug administration apparatus. Female coupling 135 can be connected to suction apparatus. Switch 136 allows for the selection of individual electrodes in a manner that is responsive to the judgment of medical or veterinary personnel. Port 131, port 132, female couplings 133, 134, 135 and switch 136 are all included on the hand set 137 to allow easy operation.

First Method of Operation

Figure 2A:
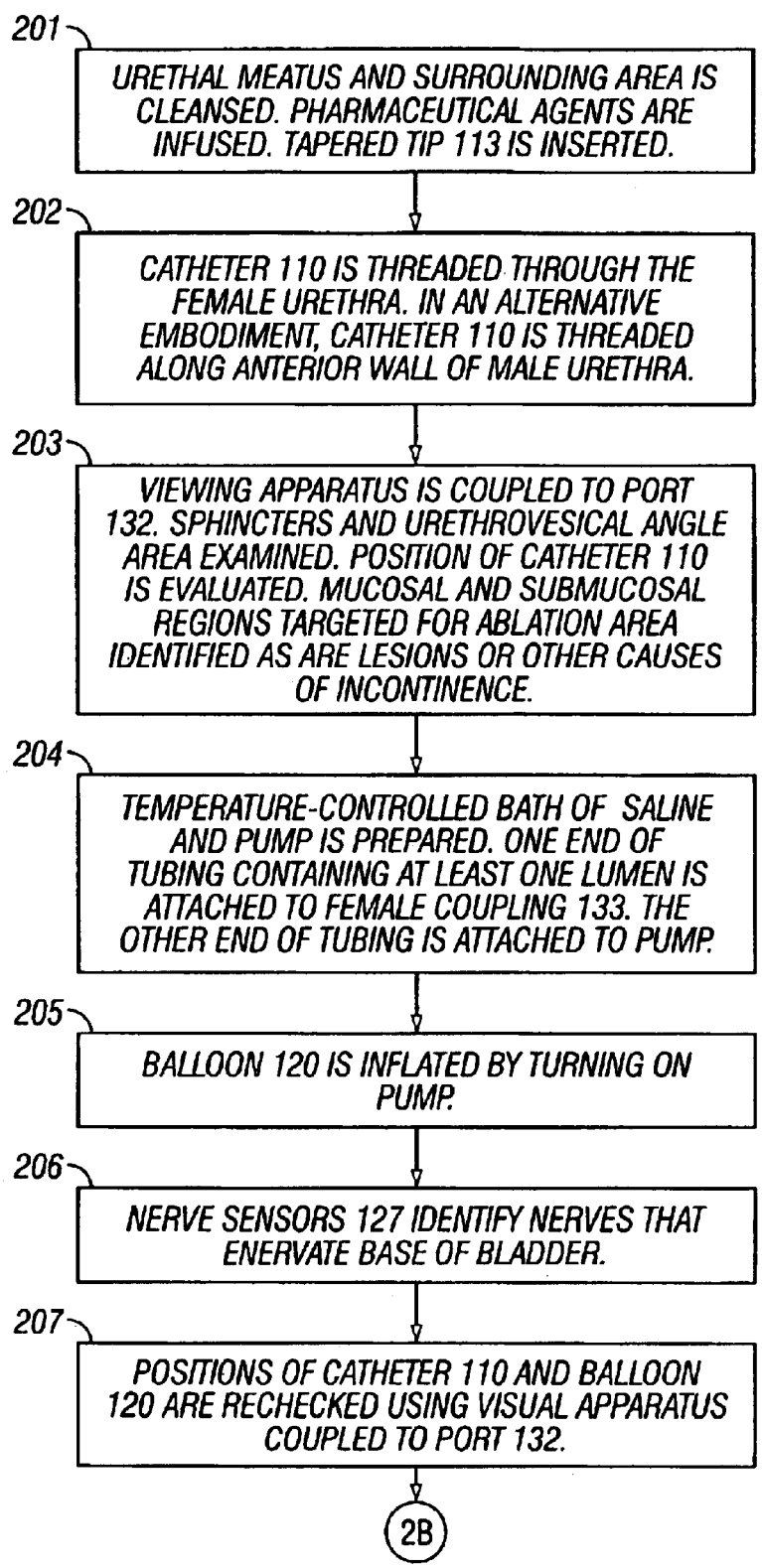
FIG. 2 is a process flow diagram of a method for treatment for urinary incontinence.
Figure 2B:
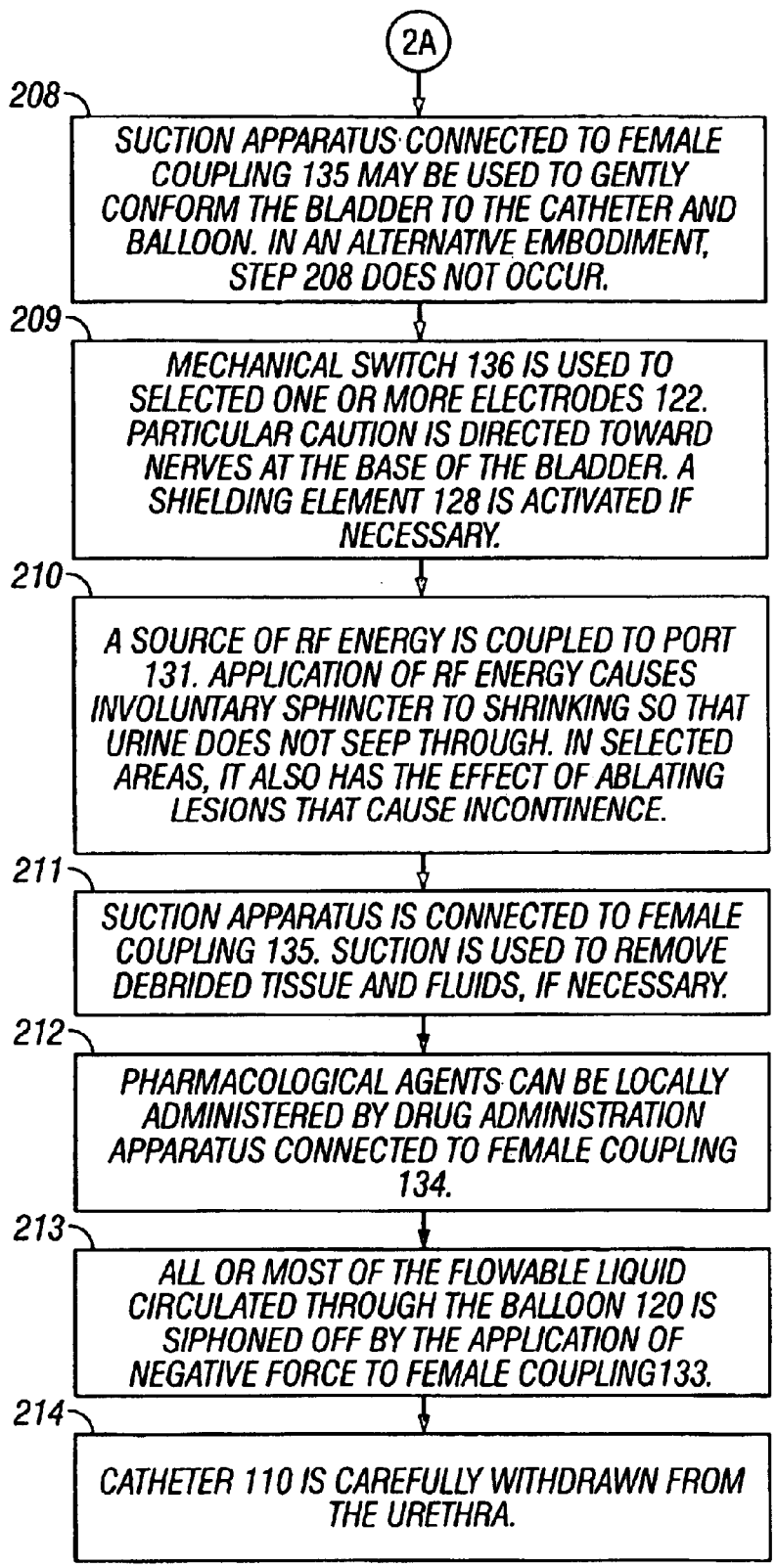

FIG. 2 is a process flow diagram of a method for treatment for urinary incontinence.

This method of operation is appropriate for the type of incontinence common to many post-menopausal parous women. In some women, the structure of the pelvic support of the bladder is damaged, either by parturition or urethral atrophy caused by estrogen deprivation. When this occurs, the urethra shortens, and the normal urethovesical angle is lost. The goals of this method of operation include producing uniform shrinkage of submuscosal tissue. This shrinkage helps restore the urethovesical angle that is important for closure of the urethral sphincter.

This method of treatment is also appropriate when incontinence is caused by inflammatory lesions of the muscosal tissue in the trigone area of the bladder. These lesions can cause uncontrollable detrusor contractions and unwanted passage of urine, often called urgency incontinence. The goals of this method include shrinkage of muscosal tissue and ablation of the lesions causing incontinence. Other possible uses of this device in the urinary tract include removal of urethral obstructions.

A method 200 is performed using a catheter and electrode assembly 100. The preferred size of the catheter 110 will be responsive to the orifice through which the catheter is inserted. The choice of pharmaceutical agents to be infused prior to or during treatment will be responsive to judgments by medical or veterinary personnel and may include lubricants, anesthetics, antispasmodics, anti-inflammatories, antibiotics or other agents.

In a step 201, the area around the urethral meatus is cleansed. The tapered tip of the catheter 110 is well lubricated and introduced into the urethral meatus in an upward and backward direction, in much the same way one would introduce a Foley catheter. Due to the potential for inducing pain, the outer opening of the urethra may be pretreated with a topical anesthetic before insertion and a muscle relaxant may be administered. The choice of pharmaceutical agents to be infused prior to or during treatment will be responsive to judgments by medical personnel and may include lubricants, anesthetics, antispasmodics, anti-inflammatories, antibiotics or other agents. In an alternative embodiment, the area of the glans penis around the urinary meatus is washed with a cleansing agent such as benzalonium chloride and the lubricated tapered tip 113 of the catheter 110 is inserted.

In a step 202, the catheter 110 is threaded through the female urethra until the tapered tip 113 and the inflatable, microporous balloon 120 extend past the neck of the bladder. Strict aseptic technique is maintained during this step and all subsequent ones. In an alternative embodiment, the catheter is threaded along the anterior wall of a male urethra.

In a step 203, viewing apparatus coupled to port 132 is used to (1) examine the sphincters and the urethrovesical angle (2) determine which areas of the mucosal or submucosal tissue are targeted for shrinkage and which lesions, if any, are targeted for ablation and (3) evaluate the position of the catheter 110. In male patients, attention is directed toward identifying evidence of lesions or other damage caused by prior surgery, such as prostatic surgery, because this is frequently the cause of incontinence in men.

In a step 204, a temperature controlled bath of cool sterile, saline or other flowable substance is prepared. One end of tubing containing at least one lumen, is attached to female coupling 133; the other end of the tubing is attached to a pump which is submerged in the temperature controlled saline bath. Double lumen tubing permits constant circulation of the flowable substance throughout the balloon 120. The nature, temperature and amount of flowable substance are responsive to judgments by medical personnel.

In a step 205, the balloon 120 is inflated by turning on the pump. Inflation of the balloon 120 serves several purposes. In addition to preventing thermal damage by providing a cool surface, it also snugly positions the electrode 122 against the wall of the bladder and helps anchor the catheter 110 in place. In an alternative embodiment, a blocking element 120a is used to help seal off the bladder neck. The blocking element may be a second balloon or a sponge, the blocking element being disposed to present a liquid-tight seal in a region proximal to said selected location.

In a step 206, the parasympathetic and sympathetic nerves that ennervate the base of the bladder are identified using the nerve sensors 127.

In a step 207, the position of the catheter 110 and the balloon 120 is checked again using the visual apparatus coupled through port 132. Any correction to the position of the catheter 110 is made at this time by repeating steps 202 through 206.

In a step 208, suction apparatus connected to female coupling 135 may be used to gently help conform the bladder to the catheter and balloon. This step is optional.

In a step 209, one or more electrodes 122 are selected for activation. Since the goal of treatment includes uniform shrinkage of the submucosal or mucosal tissue, the selected electrodes 122 usually adhere to a uniform pattern. However, when the goal is ablation of lesions, the selected electrodes need not adhere to any pattern. Particular caution is given with respect to the nerves identified in step 207. There may be instances in which these nerves are to be completely shielded from RF energy using nerve shield 128; conversely, there may be cases in which these nerves require application of RF energy. The number and pattern of selected electrodes 122 is responsive to judgement of medical personnel. The mechanical switch 136 is used to select one or more electrodes 122.

In a step 210, a source of RF energy is coupled to port 131. RF energy is provided to the electrodes 122 to shrink the targeted tissue and ablate lesions in the bladder, if present. In a preferred embodiment, the RF energy has a frequency between 435 kilohertz and 485 kilohertz. The RF energy is received by the tissues immediately near the electrodes for a period of time less than ten minutes. During this time, the adjacent tissues are cooled by the constant circulation of saline through the balloon. The duration of time and frequency of energy are responsive to judgments of medical personnel. Application of RF energy causes the involuntary sphincter to shrink so that urine does not seep through. In selected areas, it also has the effect of ablating lesions that cause incontinence. In alternative embodiments, the electrodes may deliver other forms of energy, such as heat, microwaves, infrared or visible laser energy. In other alternative embodiments, the electrodes are controlled by a feedback technique using at least one sensor such as temperature sensor 125, impedance sensor 126 or nervous activity sensor 127.

To perform ablation, the tissue is heated for a short period of time until ablation occurs. Application of RF energy causes cell death by dehydration or denaturation of cellular proteins.

To perform expansion, plumping, or shaping, the tissue is suffused with a flowable substance, such as a gas or liquid, a collagen, or another substance that can be absorbed by the body structure or tissue. The flowable substance can be exuded from the catheter, either using a separate flow line, or using the electrodes themselves. In a preferred embodiment, the tissue is heated for a short time, and thereafter cooled, so as to cause the flowable substance to crosslink or otherwise transform into a bulking, plumping, or shaping agent.

To perform coating, the flowable substance can be exuded so as to adhere to (or be adsorbed by) an epithelial layer of cells. In a preferred embodiment, the tissue is heated for a short time, and thereafter cooled, so as to cause the flowable substance to crosslink or otherwise transform into a solid mass coating or covering the epithelial layer.

To perform shrinking, the tissue is suffused with the flowable substance, with the flowable substance being selected so as to act as a receiving antenna or dielectric for the RF energy. RF energy is applied, which is differentially absorbed by the flowable substance; this causes the flowable substance to heat and to shrink the tissue it suffused, either by cell death, dehydration, or denaturation of cellular proteins.

In a step 211, suction apparatus is connected to female coupling 135; suction is applied to remove debrided tissue and body fluids, if necessary.

In a step 212, pharmacological agents can be administered locally using drug administration apparatus connected to female coupling 134. The type and dosage of drug to be administered is responsive to judgments by medical and veterinary personnel.

In a step 213, all or most of the flowable liquid circulating through the balloon 120 is siphoned off by removing the tubing from the saline bath and applying negative force to female coupling 133. This has the effect of deflating balloon 120.

In a step 214, the catheter 110 is carefully withdrawn from the urethra.

Figure 3A:
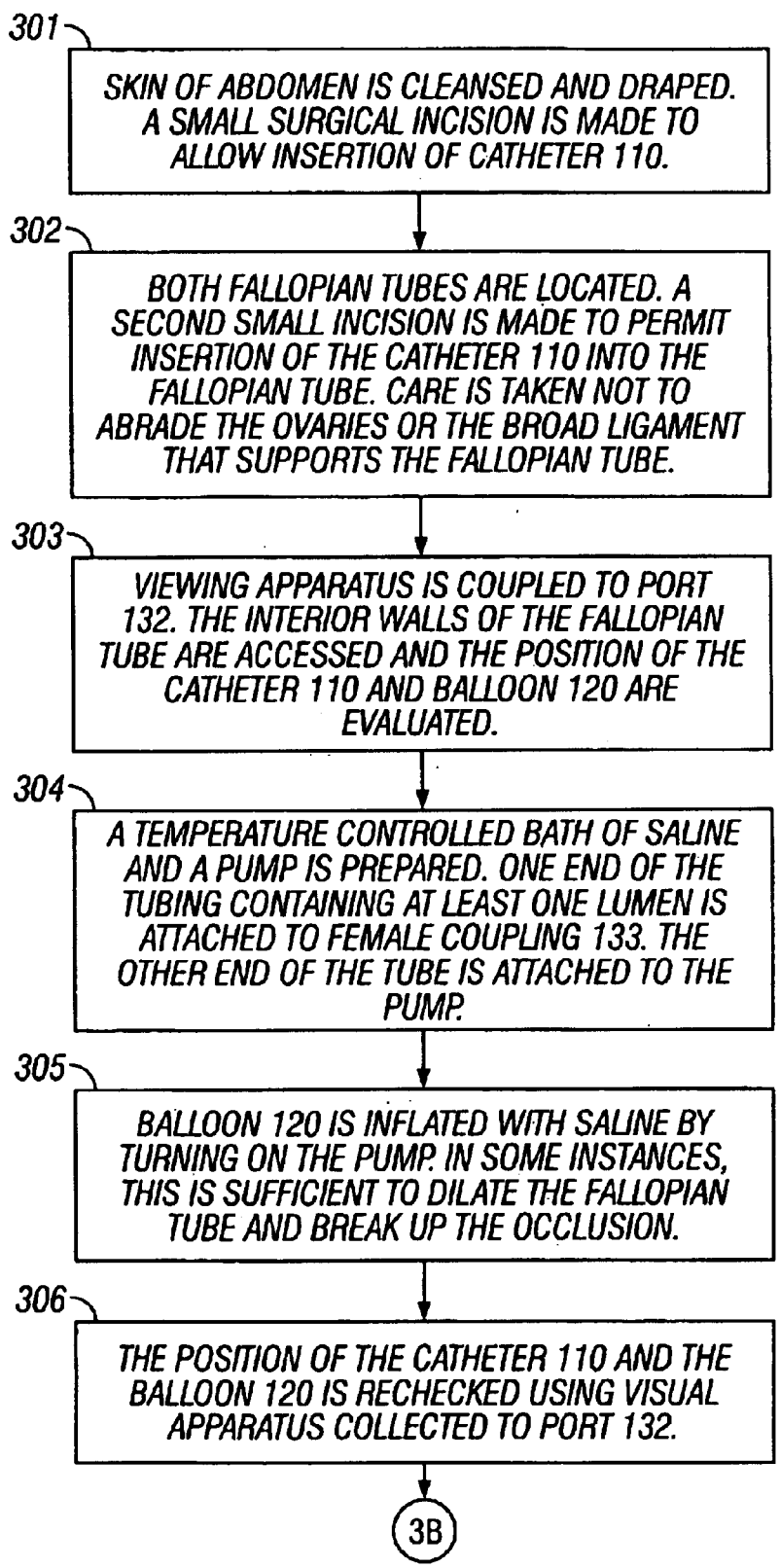
FIG. 3 is a process flow diagram of a method for treatment of an occluded fallopian tube.
Figure 3B:
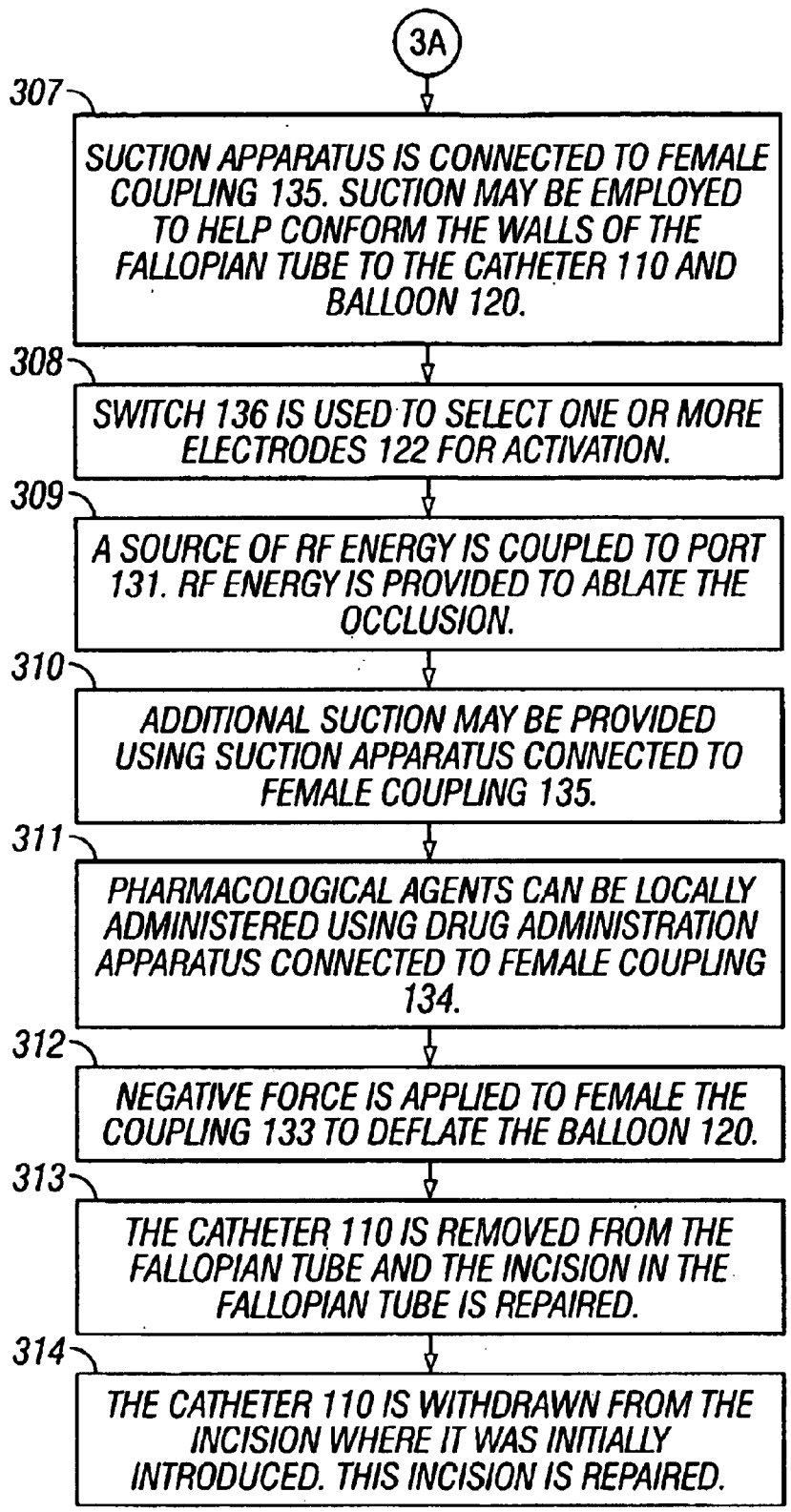

FIG. 3 is a process flow diagram for a method of treating an occluded fallopian tube.

Blockage of the fallopian tube is a frequent cause of infertility in women of reproductive years. Diagnosis of tubal blockage is generally made by hysteroslpingogram and diagnostic laparoscopy. The goals of this method of treatment include restoration of the fallopian tube patency. Other possible uses of this device in the female reproductive system include removal of uterine tumors and fibroids, and endometrial ablation.

A method 300 is performed using a catheter and electrode assembly 100.

In a step 301, the skin of the lower abdomen is cleansed and draped. A small surgical incision is made to allow the insertion of the catheter 110. Strict aseptic technique is maintained during this step and all subsequent ones. Due to the potential for inducing pain, the surface of the skin may be pretreated with a topical anesthetic before insertion. A mild anesthetizing agent such as VerSed may be indicated. The choice of pharmaceutical agents to be infused prior to or during treatment will be responsive to judgments by medical or veterinary personnel and may include lubricants, anesthetics, antispasmodics, anti-inflammatories, antibiotics or other agents.

In a step 302, both fallopian tubes are located. A second small incision is made in the wall of one the fallopian tubes to permit insertion of the catheter 110. Care is taken not to abrade the ovaries or damage the broad ligament that supports the fallopian tube.

In a step 303, viewing apparatus coupled to port 132 is used to examine the interior walls of the fallopian tube, search for occlusions, evaluate the position of the catheter 110 and balloon 120, and determine which areas are targeted for ablation.

In a step 304, a temperature controlled bath of cool sterile, saline or other flowable substance is prepared. One end of a piece of double-lumen tubing is attached to female coupling 133; the other end of the tubing is attached to a pump which is submerged in the temperature controlled saline bath. Double lumen tubing permits constant circulation of the flowable substance throughout the balloon 120. The nature, temperature and amount of flowable substance are responsive to judgments by medical personnel.

In a step 305, the balloon 120 is inflated by turning on the pump. Inflation of the balloon 120 serves several purposes. In addition to preventing thermal damage by providing a cool surface, it also anchors the catheter 110 in place and causes the set of electrodes to be brought into contact with the offending occlusions and blockages. In some instances, the act of inflating the balloon may be sufficient to dilate the fallopian tube and break up the occlusion.

In a step 306, the position of the catheter 110 and the balloon 120 is checked once again using the visual apparatus coupled through port 132. Any correction to the position of the catheter 110 is made at this time, by repeating steps 303 through 305.

In a step 307, suction apparatus connected to female coupling 135 may be used to gently help conform the interior of the fallopian tube to the catheter 110 and balloon 120. In an alternative embodiment, step 208 does not occur.

In a step 308, one or more electrodes 122 are selected for activation. Unlike the previous method, the selected electrodes 122 need not adhere to a uniform pattern. The number and pattern of selected electrodes is responsive to the judgments of medical or veterinary personnel. The mechanical switch 136 is used to select one or more of the electrodes 122.

In a step 309, a source of RF energy is coupled to port 131. RF energy is provided to the electrodes 122 to ablate the targeted tissue. In a preferred embodiment, the RF energy has a frequency between 435 kilohertz and 485 kilohertz. The RF energy is received by the tissue immediately near the electrodes for a period of time less than ten minutes. The duration of time and frequency of energy are responsive to judgments of medical or veterinary personnel.

In a step 310, additional suction may be provided using suction apparatus connected to female coupling 135.

In a step 311, pharmacological agents can be locally administered using drug administration apparatus connected to female coupling 134. The type and dosage of such drugs is responsive to judgments by medical and veterinary personnel.

In a step 312, all or most of the flowable liquid circulating through the balloon 120 is siphoned off by removing the tubing from the saline bath and applying negative force to female coupling 133. Application of this negative force deflates the balloon 120.

In a step 313, the catheter 110 is removed from the fallopian tube and the incision in the fallopian tube is repaired.

In a step 314, the catheter 110 is withdrawn from the incision where it was initially introduced into the body.

Steps 301 through 314 may be repeated, if necessary, to treat occlusions on the other fallopian tube.

Figure 4A:
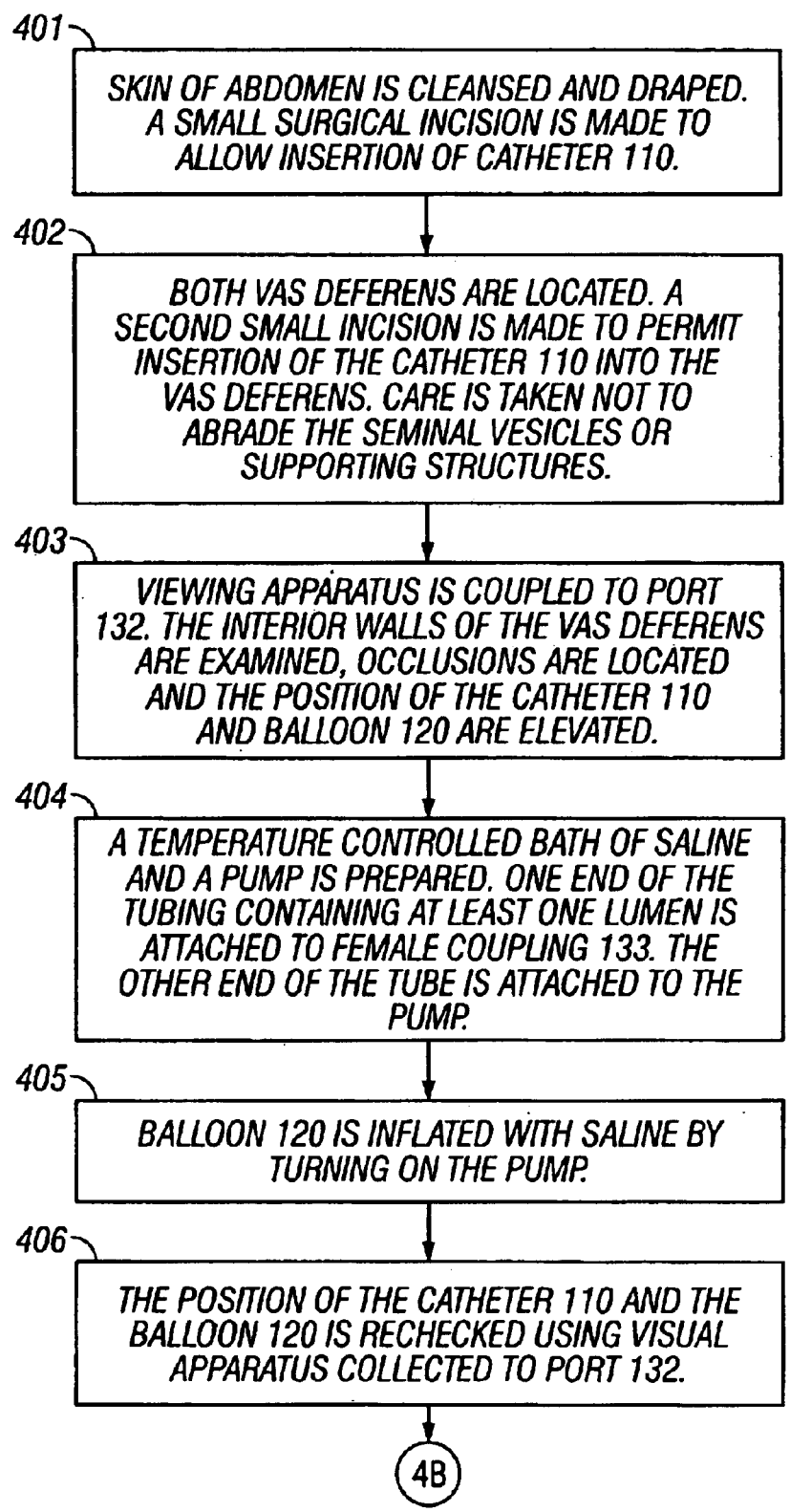
FIG. 4 is a process flow diagram of a method for treatment of an occluded vas deferens.
Figure 4B:
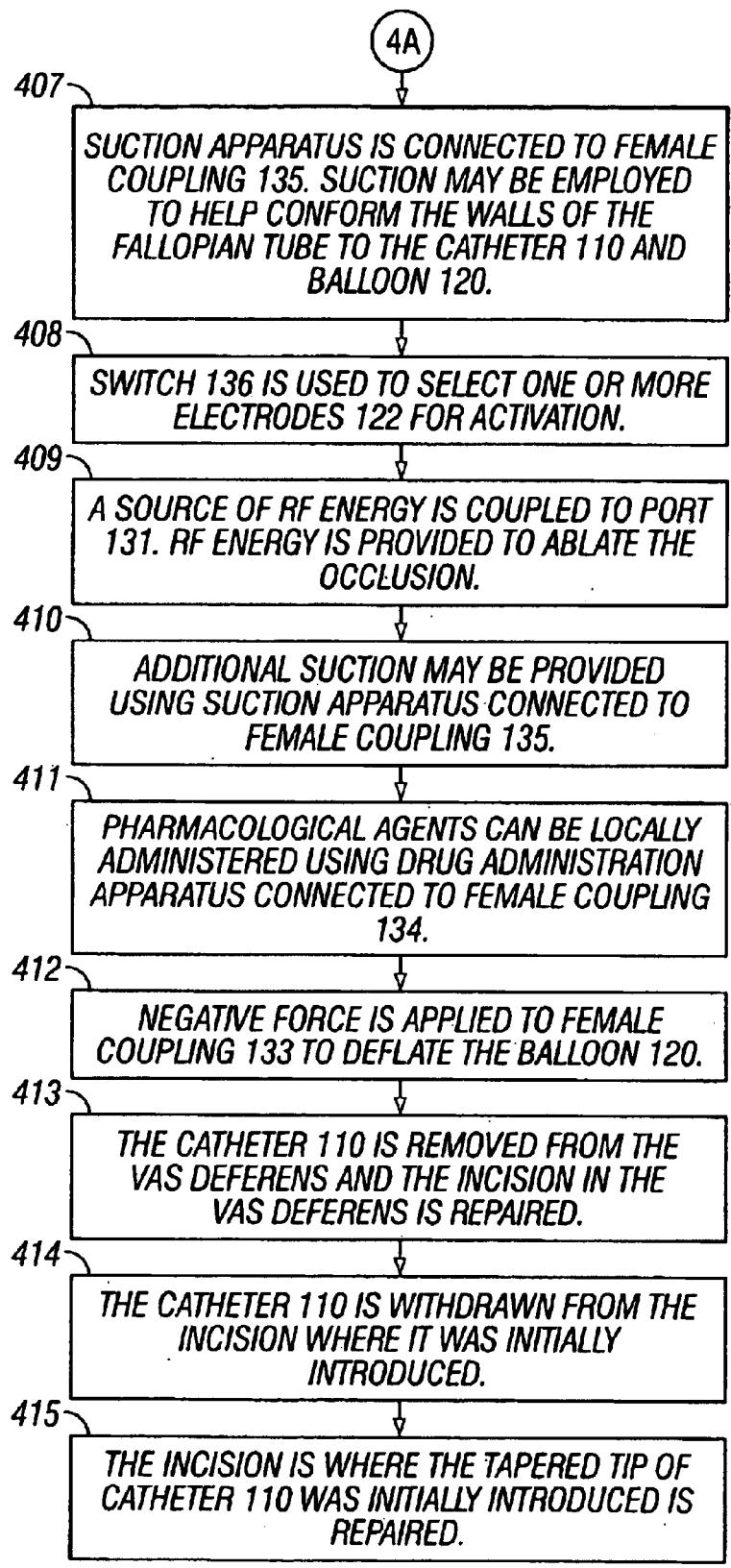

Third Method of Operation FIG. 4 is a process flow diagram of a method for treatment of an occluded vas deferens.

Obstruction of the vas deferens accounts for about 3% of male infertility. Obstruction may be congenital or acquired. Congenital obstruction may be an isolated abnormality or may be associated with cystic fibrosis. Acquired obstruction of the vas deferens may be caused by tuberculosis and gonorrhea. The goals of the method of operation include removal of the obstruction and restoration of fertility.

A method 400 is performed using a catheter and electrode assembly 100.

In a step 401, the skin of the lower abdomen is cleaned and draped. A small surgical incision is made to allow the insertion of the catheter 110. Strict aseptic technique is maintained during this step and all subsequent ones. Due to the potential for inducing pain, the surface of the skin may be pretreated with a topical anesthetic before insertion. A mild anesthetizing agent such as VerSed may be indicated. The choice of pharmaceutical agents to be infused prior to or during treatment will be responsive to judgments by medical personnel and may include lubricants, anesthetics, antispasmodics, anti-inflammatories, antibiotics or other agents.

In a step 402, both of the vas deferens are located. A second small incision is made into the wall of one the vas deferens to permit insertion of the catheter 110. Care is taken not to abrade the seminal vesicles or supporting structures.

In a step 403, viewing apparatus coupled to port 132 is used to examine the interior walls of the vas deferens, search for occlusions, evaluate the position of the catheter 110 and balloon 120, and determine which areas are targeted for ablation.

In a step 404, a temperature controlled bath of cool sterile, saline or other flowable substance is prepared. One end of a piece of double-lumen tubing is attached to female coupling 133; the other end of the tubing is attached to a pump which is submerged in the temperature controlled saline bath. Double lumen tubing permits constant circulation of the flowable substance throughout the balloon 120. The nature, temperature and amount of flowable substance are responsive to judgments by medical personnel.

In a step 405, the balloon 120 is inflated by turning on the pump. Inflation of the balloon 120 serves several purposes. In addition to preventing thermal damage by providing a cool surface, it also anchors the catheter 110 in place and causes the set of electrodes to be brought into contact with the offending occlusions and blockages. In some instances, the act of inflating the balloon may be sufficient to dilate the vas deferens and break up the occlusion.

In a step 406, the position of the catheter and the balloon is checked once again using the visual apparatus coupled through port 132. Any correction to the position of the catheter 110 is made at this time by deflating the balloon and repeating steps 303 through 305.

In a step 407, suction apparatus connected to female coupling 135 may be used to gently help conform the interior walls of the vas deferens to the catheter 110 and balloon 120. In an alternative embodiment, step 407 does not occur.

In a step 408, one or more electrodes 122 are selected for activation. The number and pattern of selected electrodes is responsive to the judgments of medical or veterinary personnel. The mechanical switch 136 is used to select one or more of the electrodes 122.

In a step 409, a source of RF energy is coupled to port 131. RF energy is provided to the electrodes 122 to ablate the targeted tissue. In a preferred embodiment, the RF energy has a frequency between 435 kilohertz and 485 kilohertz. The RF energy is received by the tissue immediately near the electrodes for a period of time less than ten minutes. The duration of time and frequency of energy are responsive to judgments of medical or veterinary personnel. Application of RF energy has the effect of ablating the offending occlusions.

In a step 410, suction may be applied, if necessary.

In a step 411, pharmacological agents may be administered locally using drug administration apparatus connected to the female coupling 134. The type of drug and dosage are responsive to judgments of medical or veterinary personnel.

In a step 412, all or most of the flowable liquid circulating through the balloon 120 is siphoned off by removing the tubing from the saline bath and applying negative force to female coupling 133. Application of this negative force deflates the balloon 120.

In a step 413, the catheter 110 is removed from the vas deferens and the incision in the wall of the vas deferens is repaired.

In a step 414, the catheter 110 is withdrawn from the incision where it was initially introduced into the body.

In a step 415, the incision where the catheter 110 was introduced is repaired.

Steps 401 through 415 may be repeated, if necessary, to treat occlusions on the remaining vas deferens.

Fourth Method of Operation

Figure 5A:
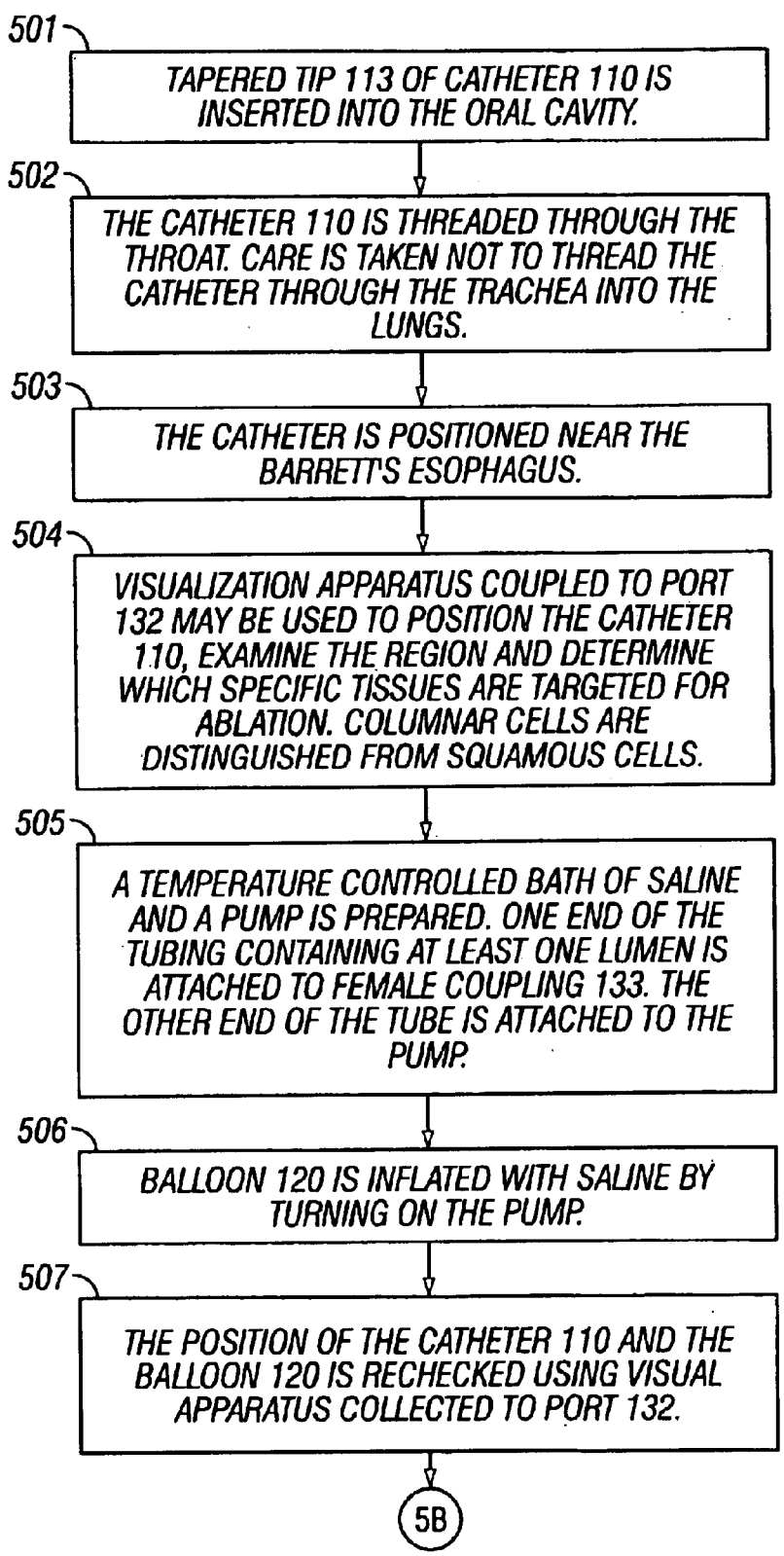
FIG. 5 is a process flow diagram of a method for treatment of Barrett's esophagus.
Figure 5B:
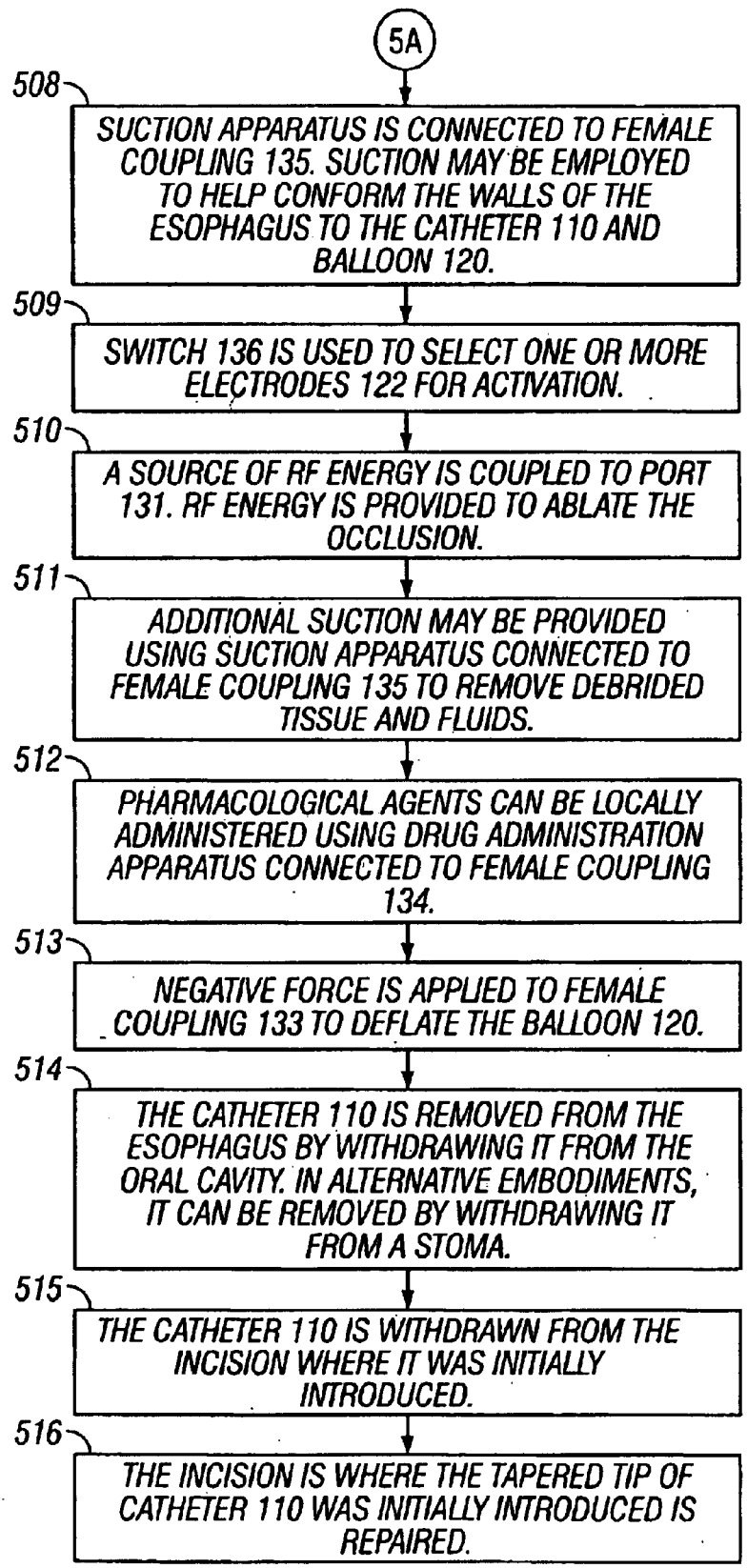

FIG. 5 is a process flow diagram of a method for treatment of Barrett's esophagus.

Barrett's esophagus often accompanies gastroesophegeal reflux disorder. It is diagnosed by esophagoscopy, which reveals the presence of columnar cells lining the lower esophagus. Adjacent peptic strictures may or may not coincide. Patients with Barrett's esophagus require close follow-up because these abnormal tissues often develop into adenocarcinoma. Other possible uses of this device in the digestive system include RF treatment of the entire gastric cardia to induce a sensation of satiety for the purpose of weight control, mapping of the electric potentials of the stomach for responsive areas when the stomach is stimulated for the purpose of weight control, removal of tumors throughout the digestive track and some disorders affecting the motility of the colon.

A method 500 is performed using a catheter and electrode assembly 100.

In a step 501, the tapered tip 113 of the catheter 110 is inserted into the oral cavity. Due to the potential for inducing pain or a gag reflex, the oral cavity is preferably pretreated with lidocaine spray or other topical anesthetic before insertion; depending upon the circumstances, a muscle relaxant may be indicated. In an alternative embodiment, the tapered tip 113 of the catheter 110 is inserted into a surgically created stoma.

The preferred size of the catheter 110 will be responsive to the orifice through which the catheter is inserted. The choice of pharmaceutical agents to be infused prior to or during treatment will be responsive to judgments by medical personnel, and may include lubricants, anesthetics, antispasmodics, anti-inflammatories, antibiotics or other agents.

In a step 502, the catheter 110 is threaded through the throat into the lower esophagus. Precautions are taken to ensure that the catheter 110 is not threaded through the trachea into the lungs.

In a step 503, the catheter 110 is positioned near the Barrett's esophagus.

In a step 504, viewing apparatus coupled to the port 132 may be used to position the catheter 110, examine the region, and determine which specific tissues are targeted for ablation. Healthy tissue composed of white squamous cells is distinguished from unhealthy pink columnar cells indicative of Barrett's esophagus.

In a step 505, a temperature-controlled bath of saline is prepared. This step is similar to step 204.

In a step 506, the balloon 120 is inflated. This step is similar to step 205. Inflation prevents thermal damage to the white squamous cells, anchors the catheter 110 in place, positions the electrodes 122 against the invasive columnar cells and prevents gas or liquids arising in the stomach from contaminating the region.

In a step 507, the exact position of the catheter 110 and balloon 120 is rechecked.

In a step 508, suction apparatus may be connected to female coupling 135. Suction may be employed to help conform the walls of the fallopian tube to the catheter and balloon 120.

In a step 509, one or more electrodes 122 are selected for activation. Since the treatment goals include ablation of the columnar cells, electrodes that are proximate to these cells are selected. The mechanical switch 136 is used to select one or more electrodes 122.

In a step 510, a source of RF energy is coupled to port 131. RF energy is provided to the electrodes so as to ablate the targeted columnar cells. In all other respects, this step is similar to step 210.

In a step 511, suction may be applied, if necessary to remove debrided tissue and body fluids.

In a step 512, pharmacological agents may be administered. This is similar to step 411.

In a step 513, the balloon 120 is deflated. This is similar to step 412.

In a step 514, the catheter 110 is removed from the esophagus by withdrawing the catheter 110 from the oral cavity. In alternative embodiments, it may be removed by withdrawing it, from a stoma.

Fifth Method of Operation

Figure 6A:
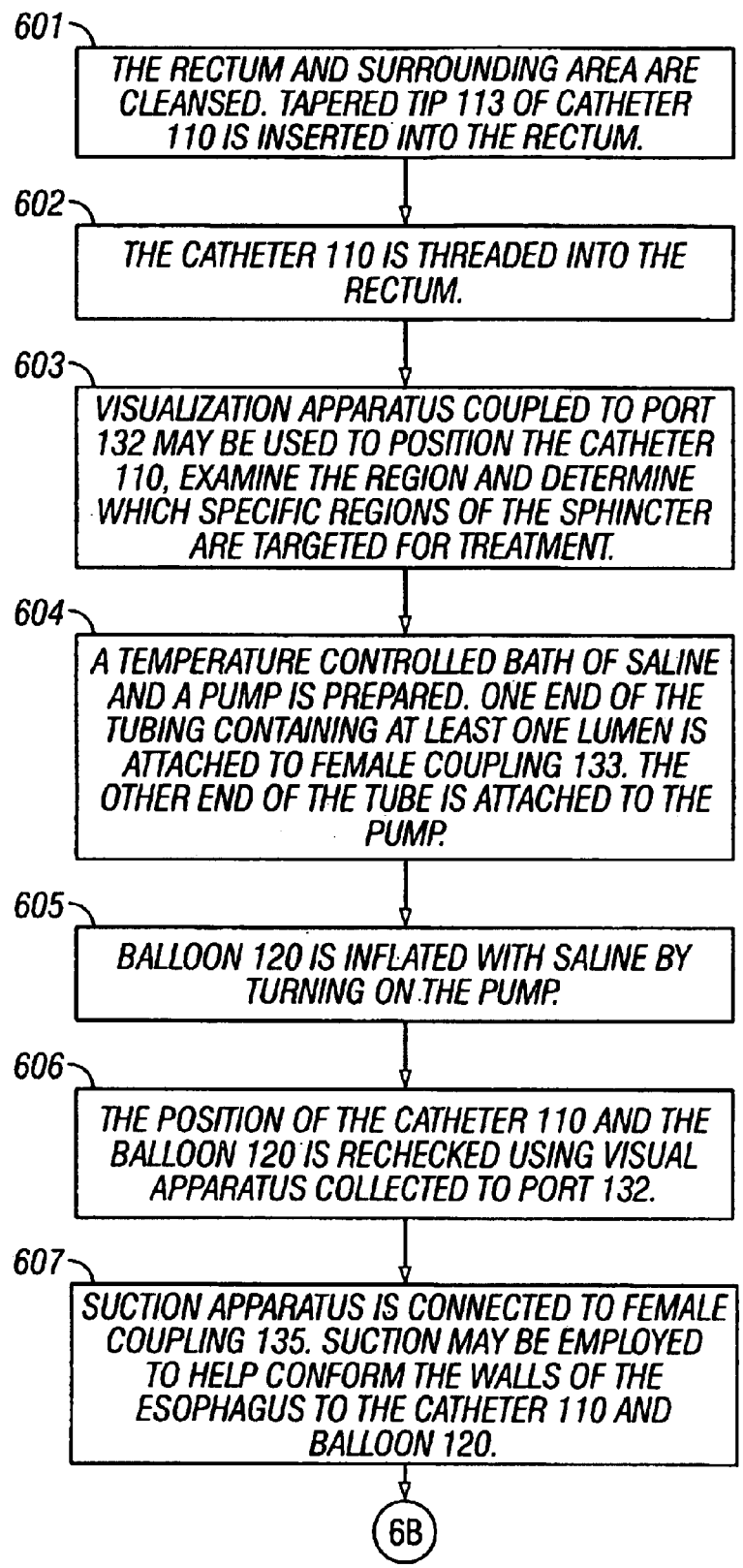
FIG. 6 is a process flow diagram of a method for treatment of a fecal incontinence.
Figure 6B:
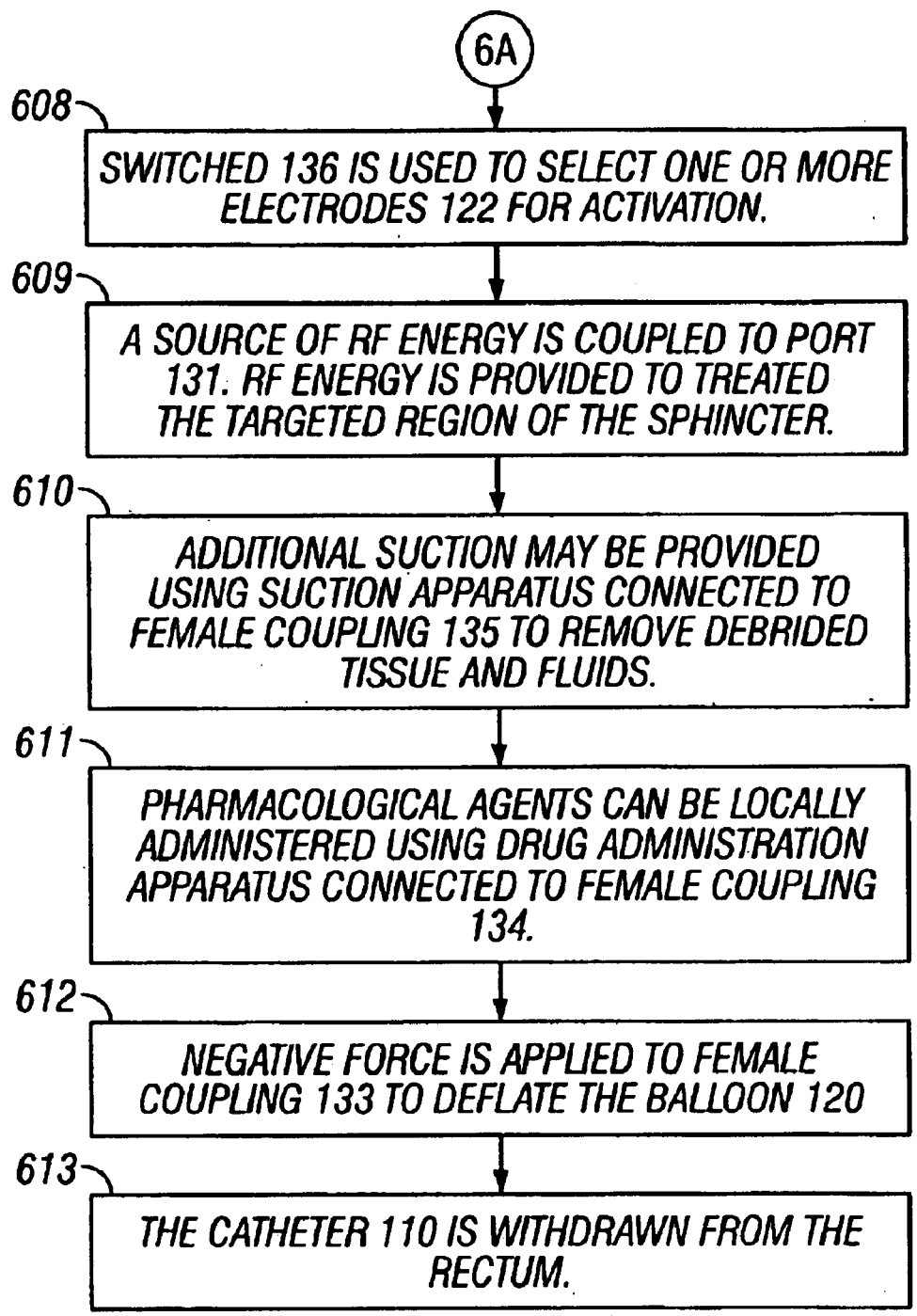

FIG. 6 is a process flow diagram of a method for treatment of fecal incontinence.

A method 600 is performed using a catheter and electrode assembly 100. The preferred size of the catheter 110 will be responsive to the orifice through which the catheter is inserted. The choice of pharmaceutical agents to be infused prior to or during treatment will be responsive to judgments by medical personnel, and may include lubricants, anesthetics, antispasmodics, anti-inflammatories, antibiotics or other agents.

In a step 601, the rectum and surrounding area are washed with a cleansing agent such as benzalonium chloride. A topical anesthetic may be applied to prevent pain associated with insertion; depending upon the circumstances, a muscle relaxant may be indicated. The tapered tip 113 of the catheter 110 is inserted into the rectum.

The preferred size of the catheter 110 will be responsive to the orifice through which the catheter is inserted. The choice of pharmaceutical agents to be infused prior to or during treatment will be responsive to judgments by medical personnel, and may include lubricants, anesthetics, antispasmodics, anti-inflammatories, antibiotics or other agents.

In a step 602, the catheter 110 is threaded into the rectum.

In a step 603, the catheter 110 is positioned near the area of the sphincter targeted for treatment. In the preferred embodiment, viewing apparatus such as an anoscope coupled to the port 132 may be used to examine the region and determine which specific tissues are targeted for treatment. It is important to distinguish between the voluntary and involuntary sphincter because fecal incontinence is frequently caused by defects in the involuntary sphincter.

In a step 604, a temperature-controlled bath of saline is prepared. This step is similar to step 204.

In a step 605, the balloon 120 is inflated. This step is similar to step 205. Inflation prevents thermal damage to the walls of the sphincter, anchors the catheter 110 in place, positions the electrodes 122 against the invasive columnar cells and prevents contamination by gas or fecal matter.

In a step 606, the position of the catheter 110 is rechecked using visual apparatus connected to port 132. Adjustments are made in the position of the catheter, if necessary.

In a step 607, suction apparatus is connected to female coupling 134. This apparatus can be used, if necessary to conform the tissue to the electrodes.

In a step 608, one or more electrodes 121 are selected for activation. This step is similar to step 209.

In a step 609, RF energy is provided to the electrodes so as to ablate the targeted tissue. This step is similar to step 210.

In a step 610, suction may be applied, if necessary to remove debrided tissue and body fluids.

In a step 611, pharmacological agents may be administered. This is similar to step 411.

In a step 612, the balloon 120 is deflated. This is similar to step 412.

In a step 613, the catheter 110 is withdrawn from the rectum.

Sixth Method of Operation

Figure 7A:
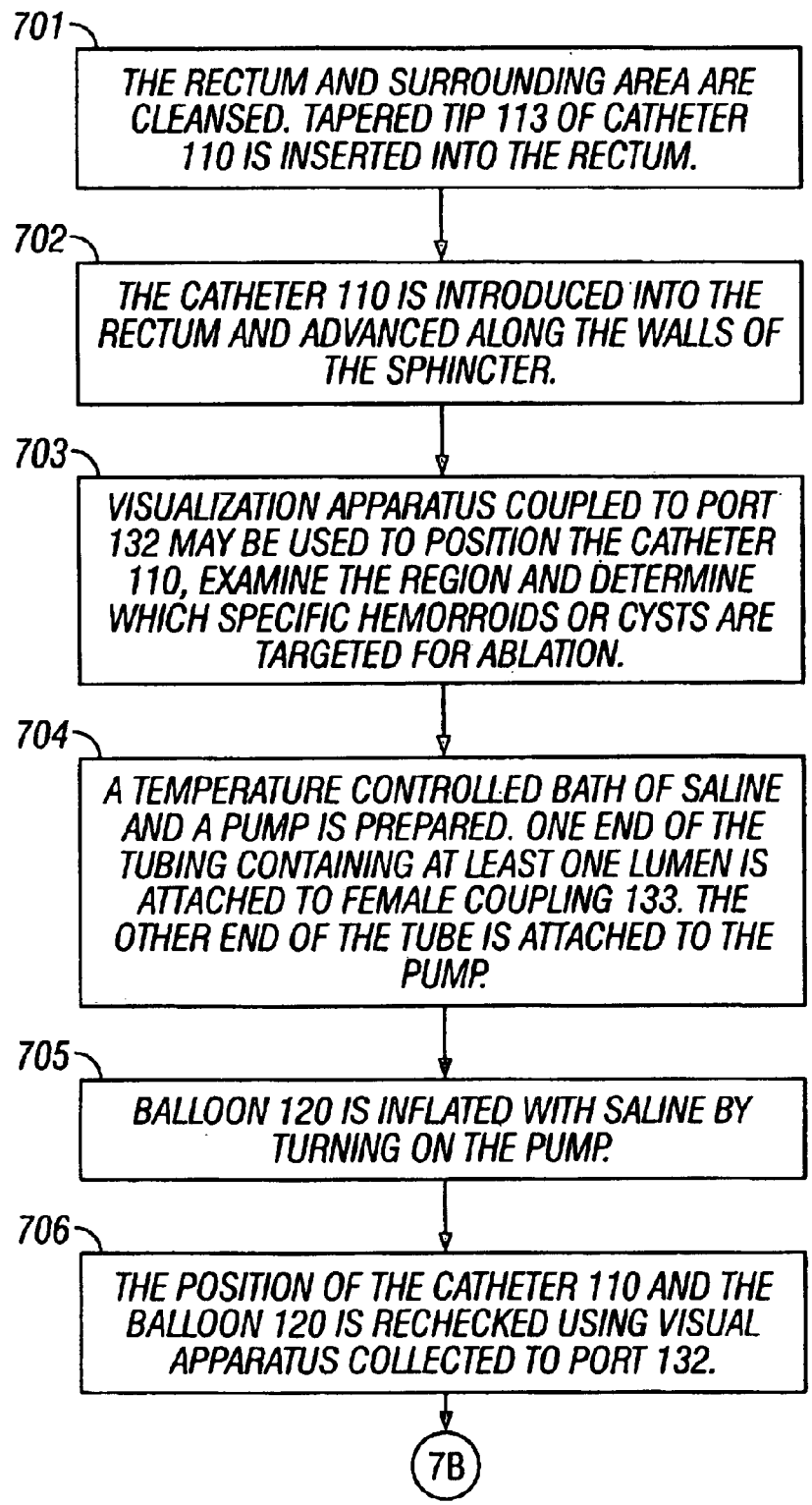
FIG. 7 is a process flow diagram of a method for treatment of a hemorrhoid or pilonital cyst.
Figure 7B:
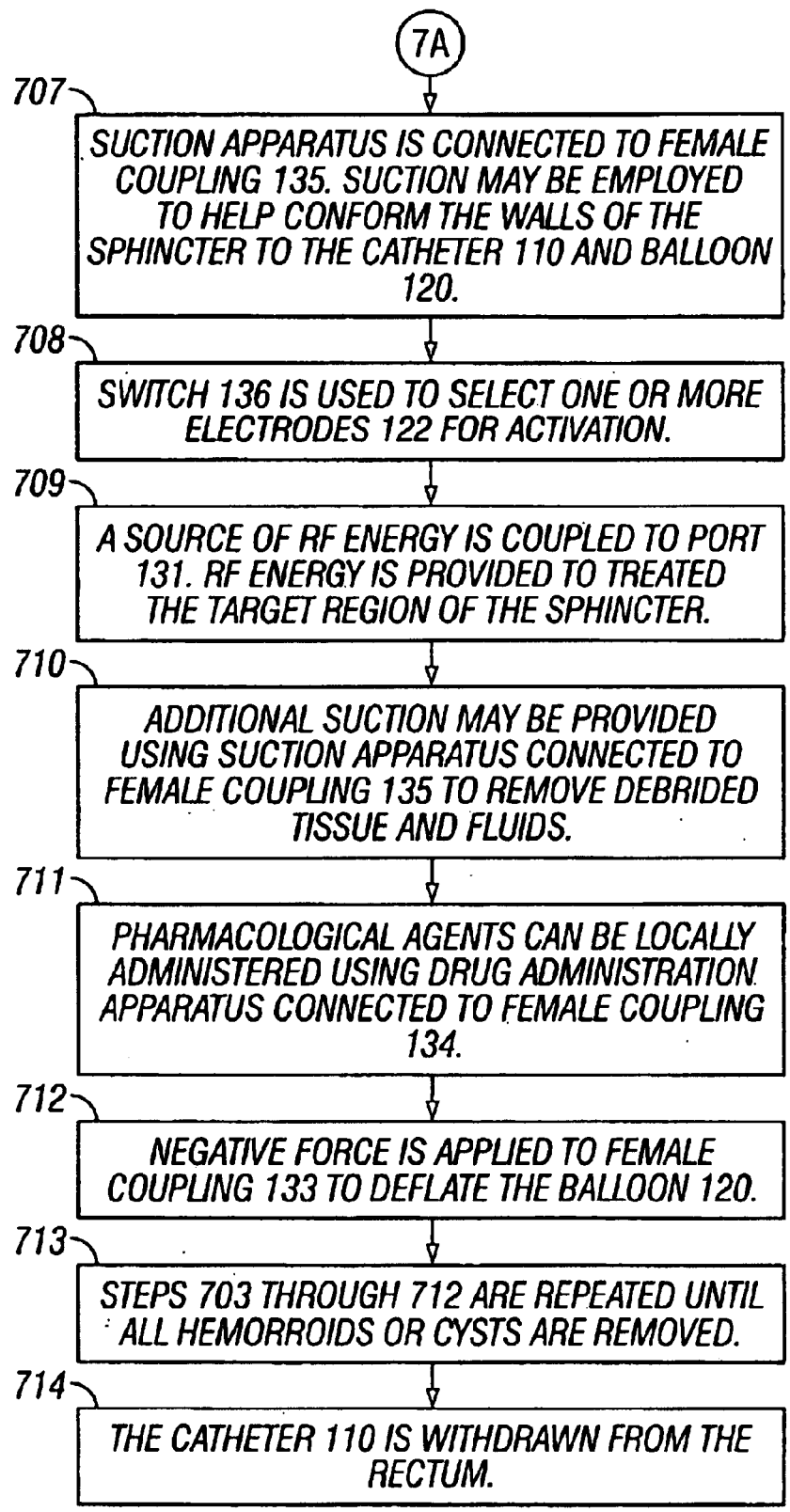

FIG. 7 is a process flow diagram of a method for treatment of a hemorrhoid or pilonital cyst.

A method 700 is performed using a catheter and electrode assembly 100.

In a step 701, the tapered tip 113 of the catheter 110 is well lubricated and the rectum and surrounding area are washed with a cleansing agent. This step is similar to step 601.

In a step 702, the catheter 110 is introduced into the rectum and advanced along the walls of the sphincter. Since hemorrhoids and pilonital cysts may occur anywhere along this passage, the distance that the catheter is introduced is responsive to the judgment of medical or veterinary personnel.

In a step 703, the catheter 110 is positioned near the internal hemorrhoid, external hemorrhoid or cyst that is targeted for ablation. In the preferred embodiment, viewing apparatus such as an anoscope is coupled to port 132. This apparatus is used to examine the region and determine which specific tissues are targeted for ablation.

In a step 704, a temperature-controlled bath of saline is prepared. This step is similar to step 204.

In a step 705, the balloon 120 is inflated. This step is similar to step 205. Inflation prevents thermal damage to the walls of the sphincter, anchors the catheter 110 in place, positions the electrodes 122 against the invasive columnar cells and prevents contamination by gas or fecal matter.

In a step 706, the position of the catheter 100 and balloon is rechecked using visual apparatus connected to port 1232. Any corrections in the positioning of the catheter 110 are made at this time, using the anoscope coupled to port 132.

In a step 707, suction: apparatus is connected to female coupling 134. This apparatus can be used, if necessary to conform the tissue to the electrodes.

In a step 708, one or more electrodes 121 are selected for activation. This step is similar to step 209.

In a step 709, a source of RF energy is coupled to port 131. This step is similar to step 210.

In a step 710, suction may be applied, if necessary to remove debrided tissue and body fluids.

In a step 711, pharmacological agents may be administered. This is similar to step 411.

In a step 712, the balloon 120 is deflated. This is similar to step 412.

In a step 713, steps 703 through 712 are repeated as necessary until all hemorrhoids or cysts are removed.

In a step 714, the catheter 110 is withdrawn from the rectum.

Seventh Method of Operation

Figure 8A:
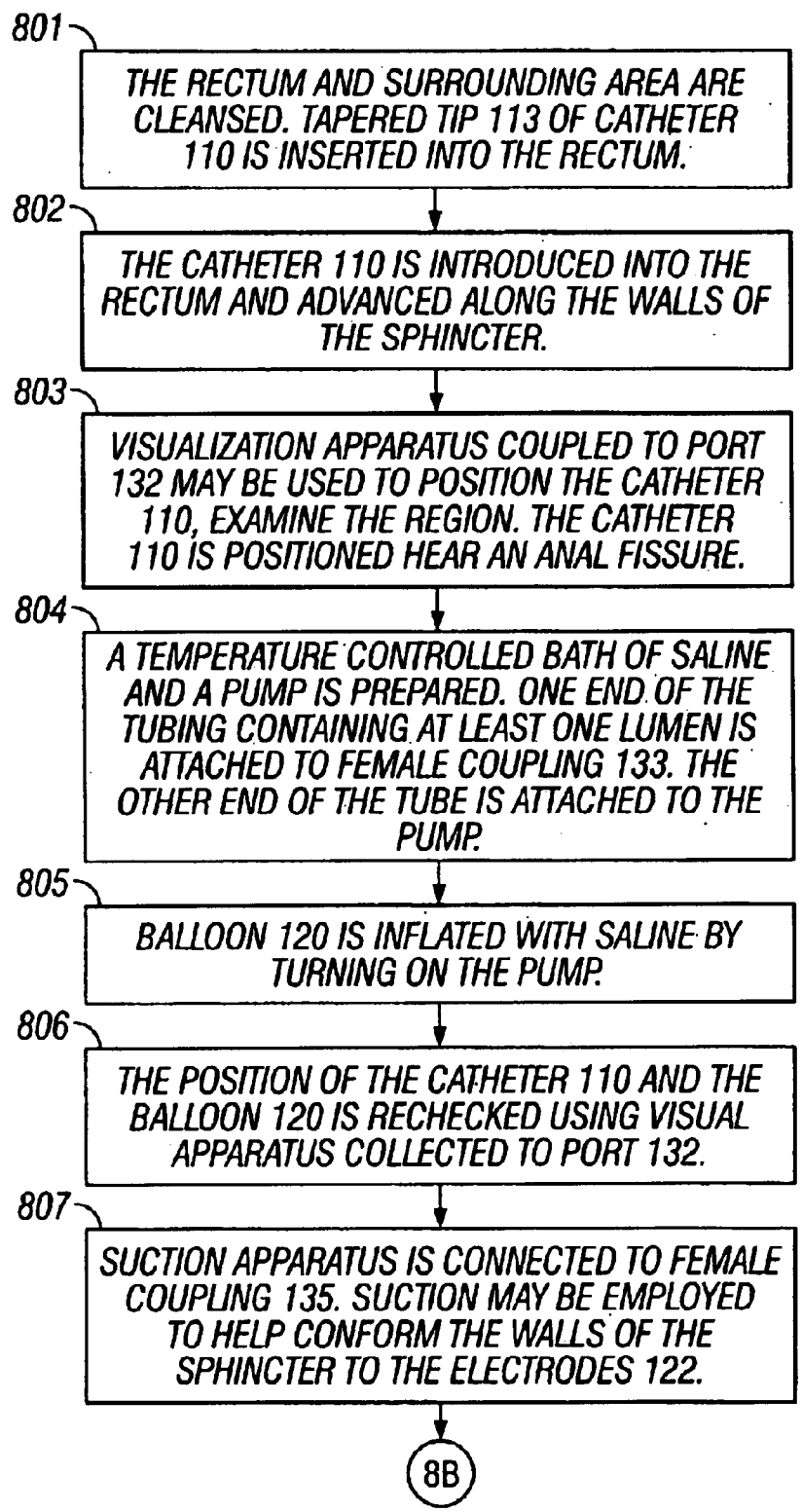
FIG. 8 is a process flow diagram of a method for treatment of an anal fissure.
Figure 8B:
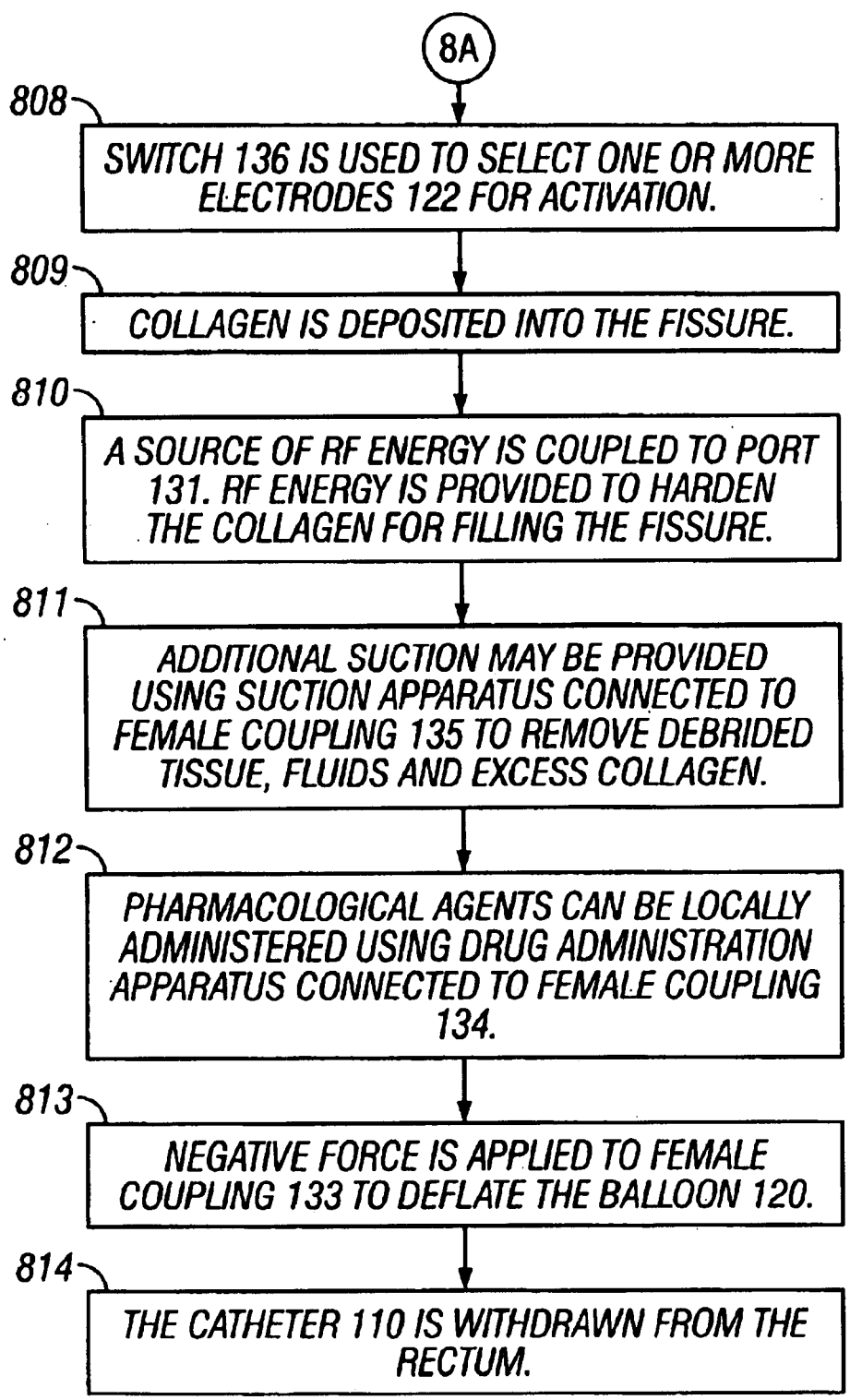

FIG. 8 is a process flow diagram of a method for treatment of an anal fissure.

A method 800 is performed using a catheter and electrode assembly 100.

In a step 801, the tapered tip 113 of the catheter 110 is lubricated and the rectum and surrounding area are washed with a cleansing agent. This step is similar to step 601.

In a step 802, the catheter 110 is introduced into the rectum and advanced along the walls of the sphincter. This is similar to step 702.

In a step 803, the catheter 110 is positioned near an anal fissure. In the preferred embodiment, viewing apparatus, such as an anoscope, is coupled to the port 132 may be used to examine the region and determine which specific tissues are targeted for ablation and where collagen should be deposited.

In a step 804, a temperature-controlled bath of saline is prepared. This step is similar to step 204.

In a step 805, the balloon 120 is inflated. This step is similar to step 205. Inflation prevents thermal damage to the walls of the sphincter, anchors the catheter 110 in place, positions the electrodes 122 against the invasive columnar cells and prevents contamination by gas or fecal matter.

In a step 806, the position of the catheter 110 and balloon 120 are rechecked. Any adjustments to the position of the catheter 110 and balloon 120 are made at this time, if necessary.

In a step 807, suction apparatus is connected to female coupling 134. This apparatus can be used, if necessary to conform the tissue to the electrodes 122.

In a step 808, one or more electrodes 122 are selected for activation. This step is similar to step 209.

In a step 809, collagen is deposited into the fissure.

In a step 810, a source of RF energy is coupled to port 131. RF energy is provided to the electrodes 121 so as to harden the collagen for filling the fissure. In a preferred embodiment, the RF energy has a frequency between 435 kilohertz and 485 kilohertz. The RF energy is received by the tissue immediately near the electrodes. The tissue is heated for a short period of time until the collagen is sufficiently hardened. In an alternative embodiment, the electrodes are controlled by a feedback technique using at least one sensor 126 such as an impedance or temperature sensor.

In a step 811, suction may be applied, if necessary to remove debrided tissue, body fluids and any excess, unhardened collagen.

In a step 812, pharmacological agents may be administered. This is similar to step 410.

In a step 813, the balloon 120 is deflated. This is similar to step 411.

In a step 814, the catheter 110 is withdrawn from the rectum.

Eighth Method of Operation

Figure 9A:
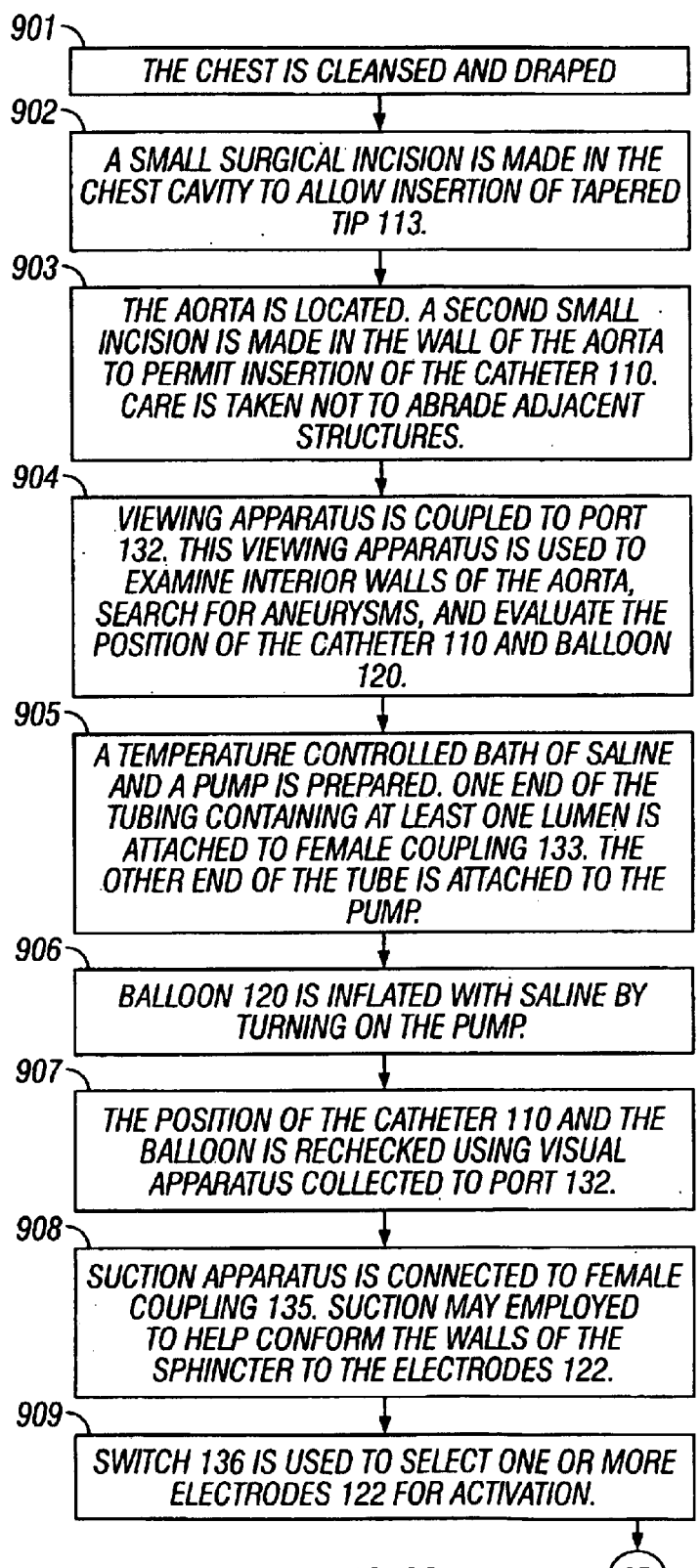
FIG. 9 is a process flow diagram of a method for treatment of an aortic aneurysm.
Figure 9B:
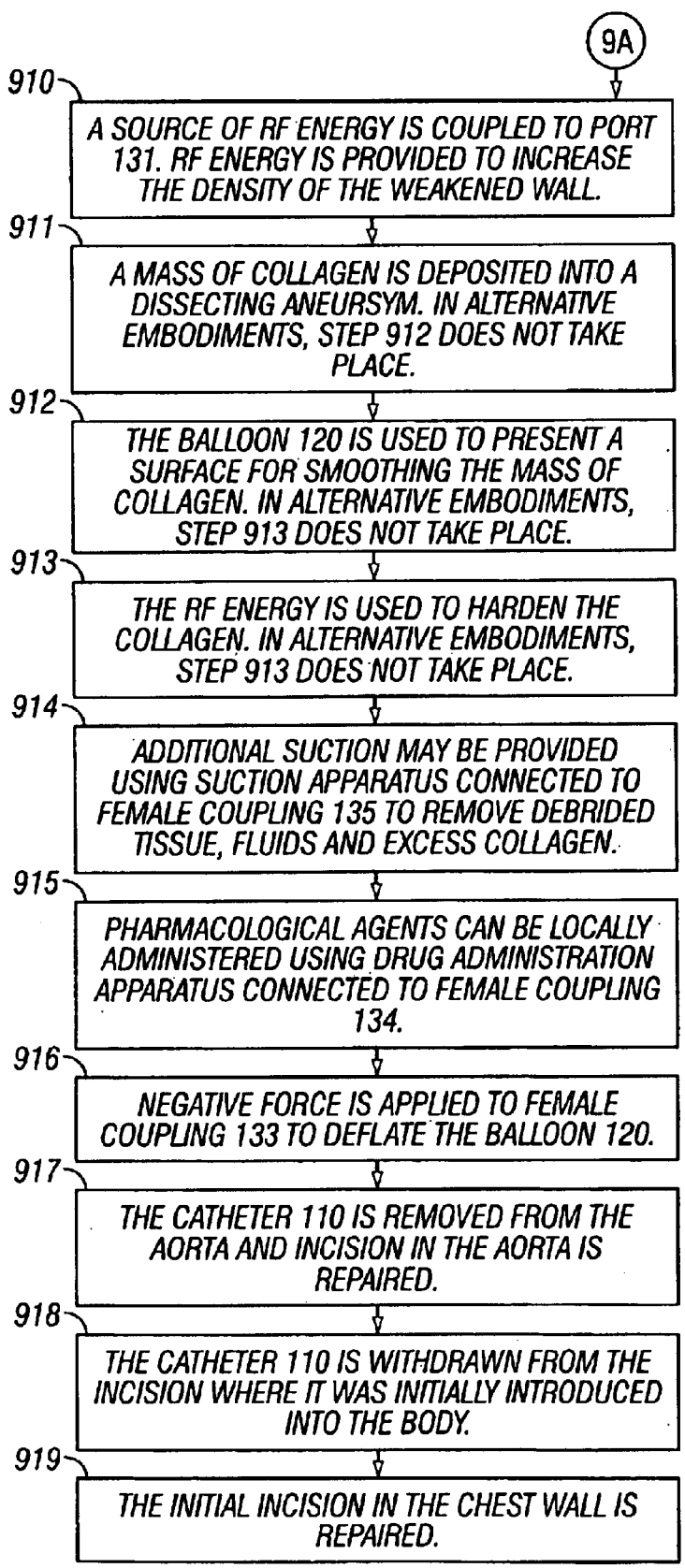
Figure 10:
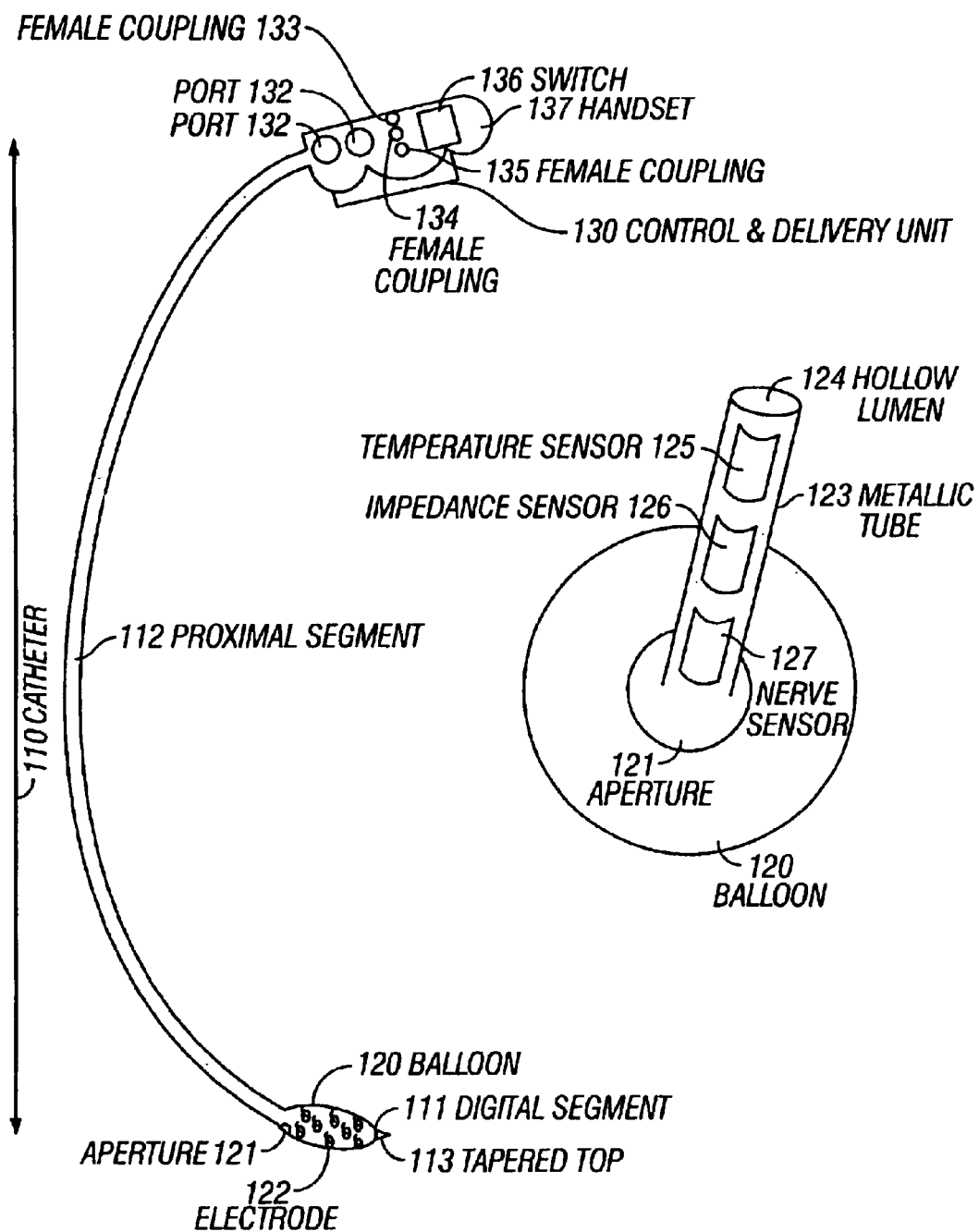
FIG. 10 shows an alternate embodiment of the system of FIG. 1.

FIG. 9 is a process flow diagram of a method for treating of an aortic aneurysm.

An aortic aneurysm involves destruction of all three layers of the aortic wall. Thinning of the wall increases the diameter of the aorta, which in turn affects the pressure on the wall. Many aneurysms, known as dissecting aneurysms, include weakened tissue that extends out from the aortic wall. In all instances, the likelihood of rupture increases with time in the absence of treatment. Although often successful, surgical treatment for aortic aneurysm is frequently avoided because of the high morbidity risk. The inventor has discovered that application of RF energy to the wall of the aorta increases the density of the wall. This increase in density has the reverse effect: the diameter of the aortic wall decreases, which in turn decreases the pressure on the aortic wall. The goals of this method of treatment include the increasing the density of the aortic wall. In alternative embodiments, a dissecting aneurysm is treated by depositing collagen into the dissecting region, smoothing over the collagen and hardening it.

A method 900 is performed using a catheter and electrode assembly 100.

In a step 901, the chest and/or abdominal region are cleansed and draped.

In a step 902, a small surgical incision is made in the chest cavity to allow the insertion of the catheter 110. Strict aseptic technique is maintained during this step and all subsequent ones. Due to the potential for inducing pain, the surface of the skin may be pretreated with a topical anesthetic before insertion. A mild anesthetizing agent such as VerSed may be indicated. The choice of pharmaceutical agents to be infused prior to or during treatment will be responsive to judgments by medical personnel and may include lubricants, anesthetics, antispasmodics, anti-inflammatories, antibiotics or other agents.

In a step 903, the aorta is located. A second small incision is made into the wall of the aorta to permit insertion of the catheter 110. Care is taken not to abrade or damage adjacent structures.

In a step 904, viewing apparatus is coupled to port 132. This viewing apparatus is used to examine the interior walls of the aorta, search for aneurysms (including dissecting aneurysms), evaluate the position of the catheter 110 and balloon 120, and determine which areas are targeted for application of RF energy.

In a step 905, a temperature-controlled bath of saline is prepared. This step is similar to step 204.

In a step 906, the balloon 120 is inflated. This step is similar to step 205. Inflation prevents thermal damage to the walls of the aortic wall, anchors the catheter 110 in place and helps position the electrodes 122.

In a step 907, the position of the catheter and the balloon is checked once again using the visual apparatus coupled through port 132. Any correction to the position of the catheter 110 is made at this time.

In a step 908, suction apparatus is connected to female coupling 134. This apparatus can be used, if necessary to gently conform the tissue to the electrodes.

In a step 909, one or more electrodes 121 are selected for activation. This step is similar to step 209.

In a step 910, RF energy is provided to the electrodes so as to increase the density of the aortic wall.

In a step 911, a mass of collagen may be deposited into a dissected aneursym. This step is optional.

In a step 912, the balloon 120 may be used to present a surface which is used for smoothing the mass of collagen. This smoothing step is performed after the mass of collagen is deposited into the aneurysm and before the mass of collagen is hardened, but in other embodiments, the mass of collagen may be hardened or softened in layers or otherwise repeatedly, so as to achieve a relatively smooth surface layer of collagen. This step is optional.

In a step 913, RF energy is applied to harden the collagen. This step is optional.

In a step 914, suction may be applied, if necessary to remove debrided tissue, body fluids and any excess, unhardened collagen.

In a step 915, pharmacological agents may be administered. This is similar to step 411.

In a step 916, the balloon 120 is deflated. This is similar to step 412.

In a step 917, the catheter 110 is removed from the aorta and the incision in the aorta is repaired.

In a step 918, the catheter I 10 is withdrawn from the incision where it was initially introduced into the body.

In a step 919, the initial incision in the wall of the chest or abdomen is repaired.

Alternative Embodiments

Although preferred embodiments are disclosed herein, many variations are possible which remain within the concept, scope and spirit of the invention, and these variations would become clear to those skilled in the art after perusal of this application.

What is claimed is:

1. Apparatus comprising:

a catheter disposed for insertion into a body at a selected location;

an inflatable, microporous balloon coupled to said catheter, said Inflatable balloon having a surface, and at least one electrode coupled proximately to said surface, said at least one electrode being capable of delivering electromagnetic energy, said at least one electrode having a hollow lumen capable of delivery of a flowable substance to said selected location, said, at least one electrode including at least one sensor disposed on the surface of the electrode for delivering electromagnetic energy from said selected location to a location outside said body; and a temperature regulator coupled to said catheter.

2. Apparatus as in claim 1, wherein said at least one electrode includes a sequence of electrodes disposed for coupling to circuits for independent control of at least a first and a second said one electrode.

3. Apparatus as in claim 1, wherein said at least one electrode include a sequence of electrodes disposed in a plurality of arrays.

4. Apparatus as in claim 1, wherein said at least one electrode include a sequence of electrodes disposed in an array.

5. Apparatus as in claim 1, wherein said catheter is disposed for either laparoscopic or manual insertion into said selected location.

6. Apparatus as in claim 1, wherein said electromagnetic energy includes RF energy at about 400 to about 500 kilohertz.

7. Apparatus as in claim 1, including a blocking element coupled to said catheter.

8. Apparatus as in claim 7, wherein said blocking element includes an inflatable balloon or a sponge, said blocking element being disposed to present a liquid-tight seal in a region proximate to said selected location.

9. Apparatus as in claim 1, wherein said sensor includes at least one of: an electromagnetic impedance sensor, an optical sensor, a temperature sensor.

10. Apparatus as in claim 1, wherein said temperature regulator includes a chilled liquid disposed proximate to said at least one surface.

11. Apparatus as in claim 1, said flowable substance being responsive to said electromagnetic energy.

12. Apparatus as in claim 11, wherein said flowable substance has a selected response to said electromagnetic energy, said selected response including receiving said electromagnetic energy for ablation, coating, expansion, plumping, shaping, or shrinking tissue.

13. Apparatus as in claim 1, wherein said at least one electrode is disposed for coupling to circuits capable of controlled application of said electromagnetic energy within an interior region of a body cavity.

14. Apparatus as in claim 13, wherein said controlled application includes uniform distribution of said electromagnetic energy in said interior region.

15. Apparatus as in claim 1, wherein said flowable substance includes at least one of:

a drug, a gas, a radioisotope, an analgesic, an antibiotic, and anti-inflammatory, an anti-spasmodic, or saline.

16. Apparatus as in claim 1, wherein said selected location is disposed within a human being or, other mammal; and said electromagnetic energy is delivered proximate to said selected location to a sphincter, to muscle tissue, or to nerve tissue.

17. Apparatus as in claim 16, wherein said sphincter or tissue is proximate to a bladder, esophagus, uterus, fallopian tube or vas deferens, sinus cavity, aorta, larynx, or pharynx.

* * * * *